«12» United States Patent
Zipp

«10» Patent No.: US 10,533,205 B1
«45» Date of Patent: Jan. 14, 2020

US010533205B1

«54» KAURENOIC ACID GLYCOSIDE PRECURSORS AND METHODS OF SYNTHESIS

«71» Applicant: Vitality Biopharma, Inc., Yuba City, CA (US)

«72» Inventor: Brandon Zipp, Davis, CA (US)

«73» Assignee: Vitality Biopharma, Inc., Yuba City, CA (US)

« * » Notice: Subject to any disclaimer, the term of this patent is extended or adjusted under 35 U.S.C. 154(b) by 789 days.

«21» Appl. No.: 14/511,103

«22» Filed: Oct. 9, 2014

Related U.S. Application Data

«60» Provisional application No. 61/888,989, filed on Oct. 9, 2013.

«51» Int. Cl.
| | |
|---|---|
| C07H 15/18 | (2006.01) |
| A61K 31/704 | (2006.01) |
| C07H 13/08 | (2006.01) |
| A61K 31/7028 | (2006.01) |
| C12P 19/44 | (2006.01) |
| C12P 19/56 | (2006.01) |

«52» U.S. Cl.
CPC ............ *C12P 19/44* (2013.01); *A61K 31/704* (2013.01); *A61K 31/7028* (2013.01); *C07H 13/08* (2013.01); *C07H 15/18* (2013.01); *C12P 19/56* (2013.01)

«58» Field of Classification Search
None
See application file for complete search history.

«56» References Cited

U.S. PATENT DOCUMENTS

| 7,807,206 B2 | 10/2010 | Magomet et al. |
| 7,927,851 B2 | 4/2011 | Brandle et al. |
| 2006/0123505 A1 | 6/2006 | Kikuchi et al. |
| 2013/0071339 A1 | 3/2013 | Markosyan |

OTHER PUBLICATIONS

In Federal Register /vol. 79, No. 241 /Tuesday, Dec. 16, 2014; Federal Register, vol. 81 No. 88, May 6, 2016 p. 27381 col. 2 and annexed examples.*
Sharma et al 2009. Chemistry and in vivo profile of ent-kaurene glycosides of Stevia rebaudiana Bertoni—An overview. Natural Product Radiance, vol. 8, Pages pp. 181-189.*
Singh et al. 2005.Stevia •The Herbal Sugar of 21st Century. Sugar Tech, vol. 7, pp. 17-24.*
Brandle.et al., (2007 Steviol glycoside biosynthesis. Phytochemistry vol. 68, pp. 1855-1863.*
Yamasaki et al. 1977. Application• of 13C Nuclear Magnetic Resonance Spectroscopy to Chemistry of Glycosides: Structures of Paniculosides-I, -II, -III, -IV, and -V, Diterpene. Glucosides of Stevia paniculata LAG. Chem. Pharm. Bulletin, vol. 25, pp. 2895-2899. (Year: 1977).*
Sakamoto et al. 1977. Application of 13C NMR Spectroscopy to Chemistry of Plant Glycosides: Rebaudiosides-D and -E, New Sweet Diterpene-Glucosides of Stevia rebaudiana BERTONI. Chem. Pharma. Bulletin, vol. 25, pp. 3437-3439. (Year: 1977).*
Chaturvedula et al. 2001. Minor diterpenoid glycosides from the leaves of Stevia rebaudiana. Phytochemistry Letters, vol. 4, pp. 209-212. (Year: 2001).*
Kamiya et al., 1979. Synthesis and Taste of Some Analogs of Stevioside, Agricultural and Biological Chemistry, vol. 43, No. 9, pp. 1863-1867. (Year: 1979).*
Visbal et al., "Carbohydrae Esters of Kaurenoic acid" Rev Latinoamer Quim vol. 32/2 pp. 68-75 (Year: 2004).*
Liu et al., "Antibacterial Diterpenoids from Saggitaria pygnnaea" Panta Medica vol. 73 pp. 84-90 (Year: 2007).*
Batista, et al. "Synthesis and trypanocidal activity of ent-kaurane glycosides," Bioorganic & Medicinal Chemistry, vol. 15 (2007) pp. 381-391.
Boeck, et al. "A Simple Synthesis of Kaurenoic Esters and other Derivatives and Evaluation of their Antifungal Activity" J. Braz. Chem. Soc., vol. 16, No. 6B, pp. 1360-1366, 2005.
Brandle and Telmer et al. "Steviol glycoside biosynthesis," Phytochemistry 68 (2007) pp. 1855-1863.
Brandle et al. "Leaf ESTs from Stevia rebaudiana: a resource for gene discovery in diterpene synthesis," Plant Molecular Biology, vol. 50, pp. 613-622, 2002 .
Daviere and Achard "Gibberellin signaling in plants" Development 140, 1147-1151 (2013).
Garcia et al. "Occurrence, Biological Activities and Synthesis of Kaurane Diterpenes and their Glycosides" Molecules 2007, vol. 12, pp. 455-483.
Kim et al. "Diterpene Glycosides from the Seeds of Pharbitis nil" J. Nat. Prod. 2009, vo. 72, pp. 1121-1127.
Kumar, H "A comprehensive analysis of fifteen genes of steviol glycosides biosynthesis pathway in Stevia rebaudiana (Bertoni)" Oct. 4, 2011, Gene 492, pp. 276-284.
Mohamed et al. "UDP-dependent glycosyltransferases involved in the biosynthesis of steviol glycosides" Journal of Plant Physiology 168 (2011) pp. 1136-1141.
Shibata, et al. "Glucosylation of Steviol and Steviol-Glucosides in Extracts from Stevia rebaudiana Bertoni" Plant Physiol. (1991) vol. 95, pp. 152-156.
Richman et al. "Functional genomics uncovers three glucosyltransferases involved in the synthesis of the major sweet glucosides of Stevia rebaudiana" The Plant Journal (2005) vol. 41, pp. 56-67.

(Continued)

*Primary Examiner* — Eric Olson
«74» *Attorney, Agent, or Firm* — Remenick PLLC

«57» ABSTRACT

Ent-kaurenoic acid glycoside precursor compositions and synthesis methods are provided. The KA-19-monoside, KA-19-bioside and KA-19-trioside precursors can be used as starting materials for a variety of kaurenoic acid based reactions. The precursors provide alternative synthesis pathways for steviol glycosides to the natural pathway based on Steviol biosynthesis. The alternative synthesis pathways using the precursors also circumvent the rate limiting step of the natural Steviol biosynthesis pathway. The precursors can be used individually or in combination to produce a mixture or individual steviol glycosides such as Rebaudioside A, Rebaudioside D or Rebaudioside M. Control over the precursor quantities and composition allows control over the composition of the resulting steviol glycosides that are finally produced.

11 Claims, 10 Drawing Sheets
Specification includes a Sequence Listing.

(56) References Cited

OTHER PUBLICATIONS

Ma et al. "Abstract for: Molecular cloning and characterization of Stevia rebaudiana UDP glucosyltransferase" Shi Yan Sheng Wu Xue Bao. Apr. 2003 vol. 36(2), pp. 123-129 (p. 1).
Takahashi et al. "The Remarkable Structural Diversity Achieved in ent-Kaurane Diterpenes by Fungal Biotransformations" Feb. 10, 2014, Molecules, vol. 19, pp. 1856-1886.
L. F. V. Bresciani et al. "Seasonal Variation of Kaurenoic Acid, a Hypoglycemic Diterpene Present in Wedelia paludosa (Acmela brasiliensis) (Asteraceae)" Hypoglycemic Activity of Kaurenoic Acid; Z. Naturforsch. 59c, pp. 229-232 (2004).

\* cited by examiner

KAURENOIC ACID GLYCOSIDE PRECURSORS AND METHODS OF SYNTHESIS

CROSS-REFERENCE TO RELATED APPLICATIONS

This application claims priority to, and the benefit of, U.S. provisional patent application Ser. No. 61/888,989 filed on Oct. 9, 2013, incorporated herein by reference in its entirety.

STATEMENT REGARDING FEDERALLY SPONSORED RESEARCH OR DEVELOPMENT

Not Applicable

INCORPORATION-BY-REFERENCE OF SEQUENCE LISTING

This application includes a sequence listing in a text file entitled "SFC6465_01A_sequence_listing.txt" created on Oct. 9, 2014 and having a 38 kb file size. The sequence listing is submitted through EFS-Web and is incorporated herein by reference in its entirety.

BACKGROUND

1. Technical Field

This technology pertains generally to synthesis schemes and biosynthetic precursors, and more particularly to ent-kaurenoic acid glycoside compositions and their production by glycosylation with glucosyltransferase enzymes. The precursors are particularly useful during the production of a variety of steviol glycoside compositions.

2. Background Discussion

The Kauranes are a class of diterpenes that are intermediates in the biosynthesis of gibberellins and steviol glycosides that have a characteristic rigid tetracyclic skeleton. Gibberellins are hormones exhibiting many biological functions and play an important role in plant physiology from seedling development to seed production. Steviol glycosides are an important non-caloric natural sweetener.

Ent-16-kauren-19-oic acid or kaurenoic acid (KA) is one of the most important Kaurane members, exhibiting a number of interesting properties, including anti-inflammatory, anthelmintic, anti-nociceptive and other characterized biological activities.

Kaurenoic acid is observed in several economically important plant species, including *Sphagneticola trilobata, Copaifera langsdorffii* (Leguminaceae), and *Stevia rebaudiana*.

In addition to gibberellin synthesis, another important secondary product of kaurenoic acid KA in plants are the sweet steviol glycosides (SGs) found in the genus *Stevia rebaudiana*. Steviol glycosides are currently extracted from plants, and with their importance as a non-caloric natural sweetener their production is projected to increase over the coming years.

The leaves of *Stevia rebaudiana* are typically processed with hot water and an aqueous extraction is used to extract and concentrate the steviol glycosides. The sweetness of the extracts of the *Stevia* plant is due to the presence of rebaudiosides and other steviol glycosides that are present. The commercial *Stevia* sweetener products that are available generally contain a majority of Rebaudioside A with lesser amounts of Stevioside, Rebaudioside C, D, and F and other glycosides.

However, the composition of extracts from *Stevia* leaves is often inconsistent between batches and dependent on the cultivation and extraction methods that are employed. The variable mixtures of steviol glycosides in extracts from plants may also contain contaminants that contribute to undesirable and inconsistent flavors in the extracts. These undesirable and inconsistent flavors present a significant obstacle to marketplace acceptance and commercialization of *Stevia* based sweeteners.

Recent attempts to improve the yield of steviol glycosides in plants include engineering the *Stevia* plant to overexpress steviol or various synthesis enzymes. However, these approaches are still susceptible to processing variations and contamination.

Therefore, there is a need for a process for the synthesis of rebaudiosides and other steviol glycosides through controlled enzymatic methods that is inexpensive and efficient.

BRIEF SUMMARY

The present technology relates to the composition of ent-kaurenoic acid glycoside precursors and their production by glycosylation with glucosyltransferase enzymes. The KA-19-monoside, KA-19-bioside and KA-19-trioside precursors can be used as starting material for a variety of kaurenoic acid based reactions.

The formation of the precursors from ent-kaurenoic acid has also been shown to improve the solubility of KA for use in aqueous applications and extraction. KA like other diterpenoids exhibits poor solubility in aqueous compositions. One way to improve the solubility of KA is to attach sugars or sugar polymers to the carboxyl group at the C19 position of the kaurenoic acid skeleton, creating a polar KA-glycoside molecule.

The utility of the precursors of the present technology is illustrated with alternative synthesis pathways for steviol glycosides to the natural pathway based on Steviol biosynthesis that the precursors provide. The precursors can be used individually or in combination to produce a mixture or individual steviol glycosides such as Rebaudioside A (Reb A), Rebaudioside D (Reb D) or Rebaudioside M (Reb M) in this illustration. Control over the precursor quantities and composition allows control over the composition of the resulting steviol glycosides that are finally produced.

The alternative synthesis pathways using the precursors also circumvent the rate limiting step of the natural Steviol biosynthesis pathway. In plants, conversion of Steviol to Steviol-13-O-monoside is thought to be the rate limiting step in steviol glycoside (SG) biosynthesis, thus creating a bottleneck in SG biosynthesis early in the pathway.

In *Stevia rebaudiana*, ent-kaurenoic acid (KA) is committed to steviol glycoside biosynthesis upon hydroxylation at C13 by kaurenoic acid hydroxylase (KAH, a.k.a. steviol synthase) and then undergoes a series of primary, secondary, and tertiary glycosylation steps on the C13 hydroxyl and C19 carboxyl groups in specific reactions catalyzed by enzymes termed UDPG-dependent glycosyltransferases (UGTs). The UGTs transfer the sugar moiety from an activated nucleotide-sugar donor such as uridine-diphosphoglucose (UDPG), creating a covalently bound sugar on the diterpenoid backbone.

In Steviol glycoside biosynthesis, glycosylation at the C13 hydroxyl and the C19 carboxyl groups are largely independent of each other, with UGTs having a gradient of activity towards substrates with varying sugar conformations at the primary and opposing site. This gradient of activity allows for glycosylation events to occur in different orders between the C13 and C19 positions as long as it follows the deposition of primary glycosylation, secondary glycosylation, tertiary glycosylation, etc.

Since the addition of sugar molecules can occur in differing orders, synthesis schemes using glycosyltransferases (UGTs) and sequences can be formulated. In one embodiment, known *Stevia* glycosyltransferases (UGTs) are used for coordinated glycosylation events. In another embodiment, glycosylation events are performed by non-*Stevia* sourced glycosyltransferases. In addition, the selection of glycosyltransferases can also be optimized for efficiency for each substrate.

Likewise, the production of the precursors from ent-kaurenoic acid (KA) can be facilitated with any glycosylation mechanism including the use of known glycosyltransferases from any source. For example, in one embodiment, the *Stevia* enzyme UGT74G1 (SEQ ID No.: 1) is used to glycosylate the carboxyl group at C19 of KA to produce a KA-19-monoside. The application of KAH to the KA-19-monoside precursor produces Steviol-19-O-monoside. The Steviol-19-O-monoside can be then converted to Rubusoside by UGT85C2, and bypass the rate-limiting step of converting steviol to steviol-13-O-monoside that is naturally catalyzed by UGT85C2 (SEQ ID No.: 7).

Furthermore, the KA-19-monoside, KA-19-bioside and KA-19-trioside precursors can be mixed in various combinations and quantities and processed simultaneously. In another embodiment, ent-kaurenoic acid (KA) is added to the precursor mixture so that the enzymatic reactions from successive enzymes take place on four different substrates simultaneously. The final composition of steviol glycosides can be controlled and determined by the selection of precursors, quantities and synthesis parameters.

Several enzymes or their functional equivalents are identified in the production of the various KA-precursors and their use in the synthesis of Steviol glycosides.

Although DNA sequences for UGT74G1 (SEQ ID No.: 2, 13 and 14), UGT76G1 (SEQ ID No.: 6, 15 and 16), UGT85C2 (SEQ ID No.: 8, 17 and 18), UGT91D2 (SEQ ID No.: 10, 19 and 20) and Os03g0702000 (SEQ ID No: 12, 21 and 22) and their products are identified, substantially identical sequences are at least 70%, 75%, 80%, 85%, 90%, 92%, 95%, 96%, 97%, 98%, or 99% identical to a given sequence.

Furthermore, any glucosyltransferase known in the art that can glucosylate the precursor molecules from any source may be employed herein. The phrase "functional equivalent" refers to any enzyme or chemical process from any source that will produce substantially the same functional results as produced by the glucosyltransferase enzymes that are identified.

According to one aspect of the technology, KA-19-monoside, KA-19-bioside and KA-19-trioside precursors are provided that have different solubility and physical characteristic from ent-kaurenoic acid and can participate in many different synthesis settings.

According to another aspect of the technology, synthesis methods are provided for producing selected rebaudioside compositions that do not use steviol as an intermediate substrate.

A further aspect of the technology is to provide synthesis methods that allow control over the type of rebaudioside or mixture of rebaudiosides that are produced and their relative percentage in the final composition.

Further aspects of the technology will be brought out in the following portions of the specification, wherein the detailed description is for the purpose of fully disclosing preferred embodiments of the technology without placing limitations thereon.

BRIEF DESCRIPTION OF THE SEVERAL VIEWS OF THE DRAWING(S)

The technology described herein will be more fully understood by reference to the following drawings which are for illustrative purposes only:

DETAILED DESCRIPTION

Referring more specifically to the drawings, for illustrative purposes an embodiment of the methods for producing ent-kaurenoic acid glycoside precursors is illustrated by their use in the selective production of steviol glycosides. The production of the precursors and one use are described and depicted generally in FIG. 1 through FIG. 6. It will be appreciated that the methods may vary as to the specific steps and sequence and the compositions may vary as to elements and sequence without departing from the basic concepts as disclosed herein. The method steps are merely exemplary of the order in which these steps may occur. The steps may occur in any order that is desired, such that it still performs the goals of the claimed technology.

Figure 1:
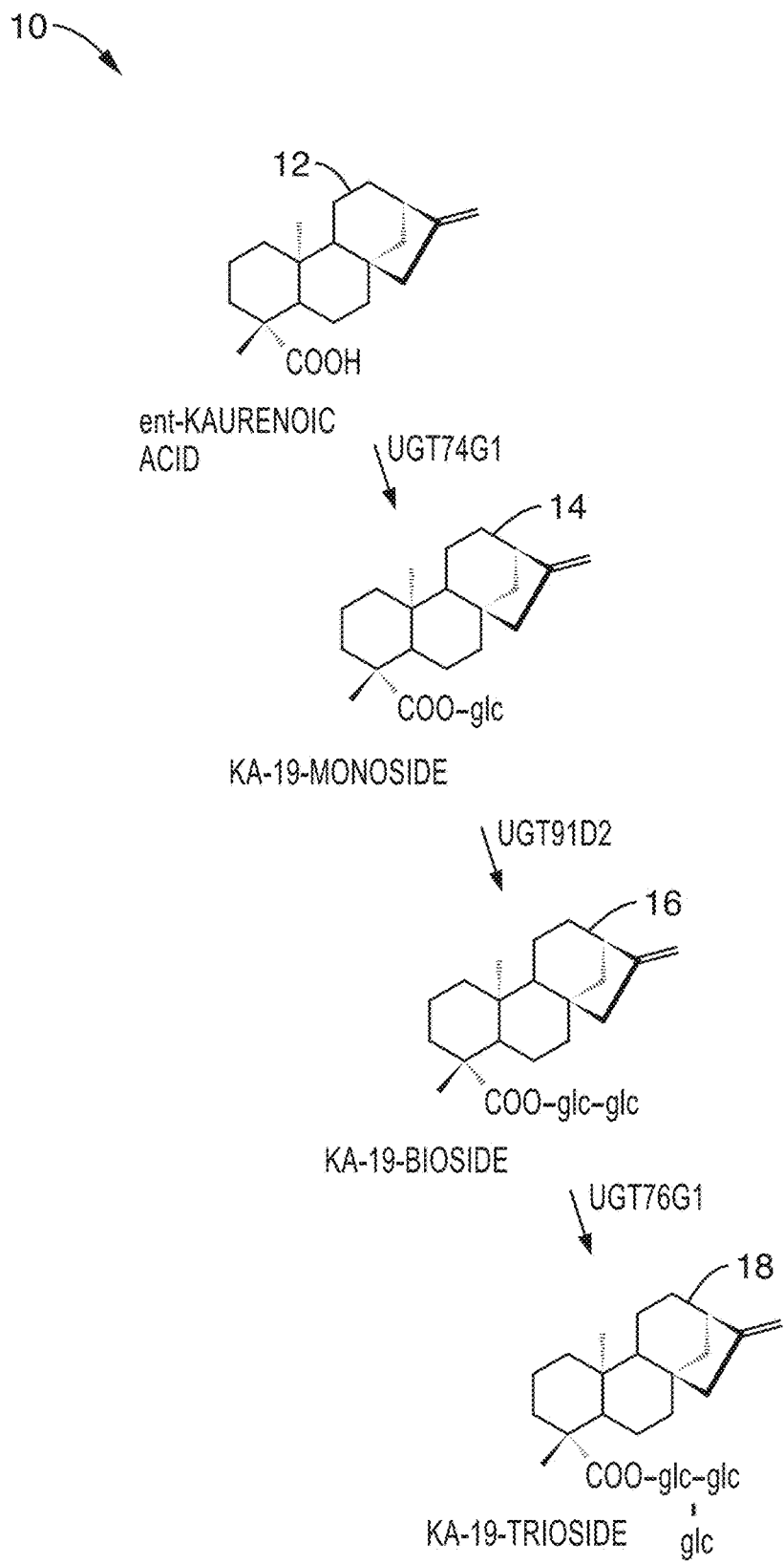
FIG. 1 is a schematic flow diagram of the synthesis of KA-19-monoside, KA-19-bioside and KA-19-trioside precursors from ent-kaurenoic acid.

The preferred synthesis methods 10 for the KA-19-monoside 14, KA-19-bioside 16 and KA-19-trioside 18 precursors from ent-kaurenoic acid 12 are shown schematically in FIG. 1.

KA-19-monoside 14 precursor is synthesized with the enzymatic transfer of a sugar from an activated sugar donor to the carboxyl group on carbon C19 of ent-kaurenoic acid (KA) 12. The glycosylation of the carboxyl group of C-19 of KA is preferably accomplished with a *Stevia* enzyme UGT74G1 (SEQ ID No.: 1) or cyclodextrin glucanotransferase. However, any enzyme or chemical process from any source that results in this glycosylation event to produce the kaurenoic-acid-19-monoglycoside precursor can be used.

Figure 2A:
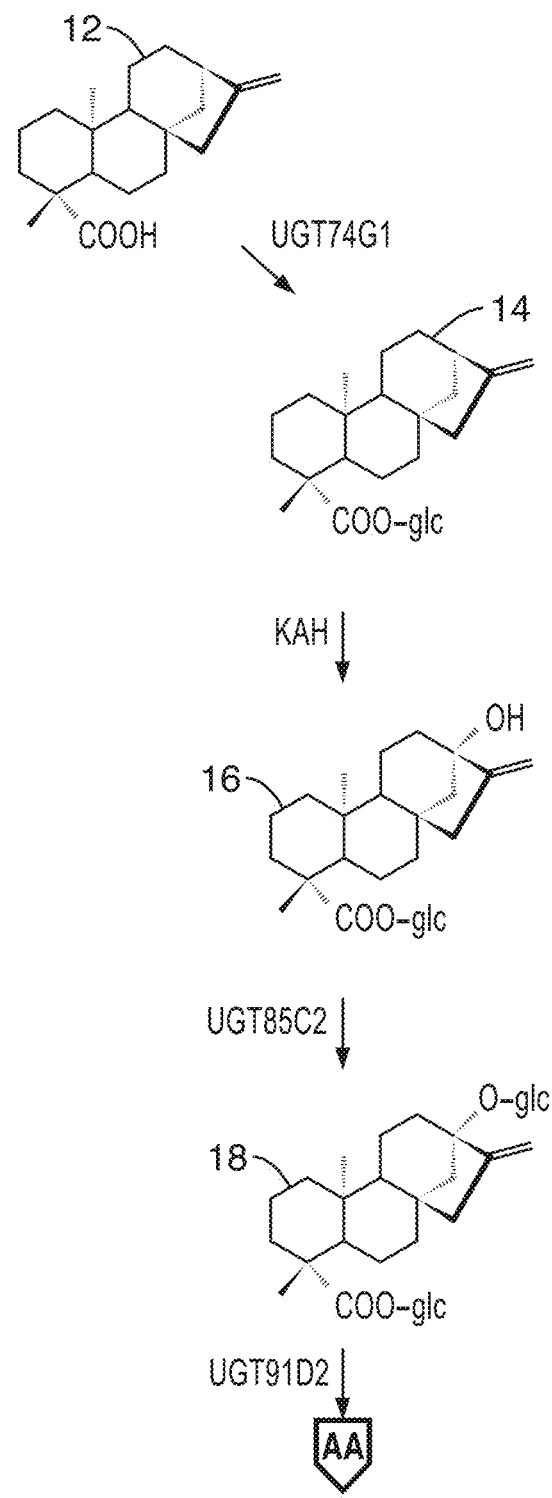
FIG. 2A and FIG. 2B depict a schematic flow diagram of the synthesis of Reb A and/or, Reb D and Reb M from the KA-19-monoside precursor according to one embodiment of the technology.
Figure 2B:
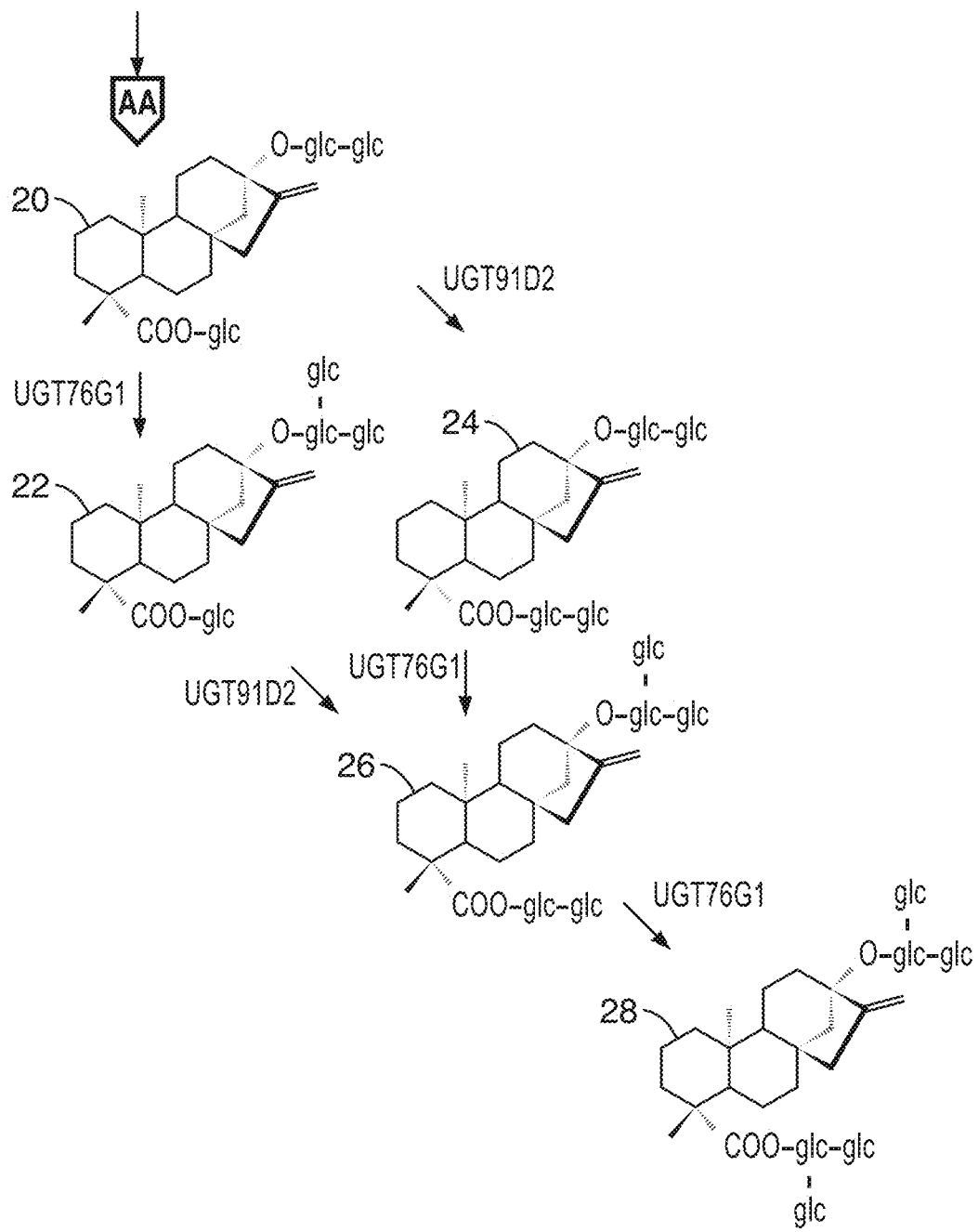

Although FIG. 1 shows that glucose is attached to the carboxyl group as the primary sugar, other sugars or modified sugars can be attached in the alternative in this glycosylation step such as fructose, xylose, and rhamnose. As illustrated in FIG. 2A and FIG. 2B, the KA-19-monoside precursor 14 can be used in many settings including an alternative biosynthetic route for steviol glycosides (Reb A) that bypasses the production of the pathway intermediate of steviol and the rate limiting step of the conversion of Steviol to Steviol-13-O-monoside.

The KA-19-bioside 16 precursor is preferably produced with the glycosylation of the primary sugar of the C19 carboxyl groups of the KA-19-monoglycoside 14 to produce the kaurenoic-acid-19-bi-glycoside (KA-19-bioside) precursor 16.

Figure 3A:
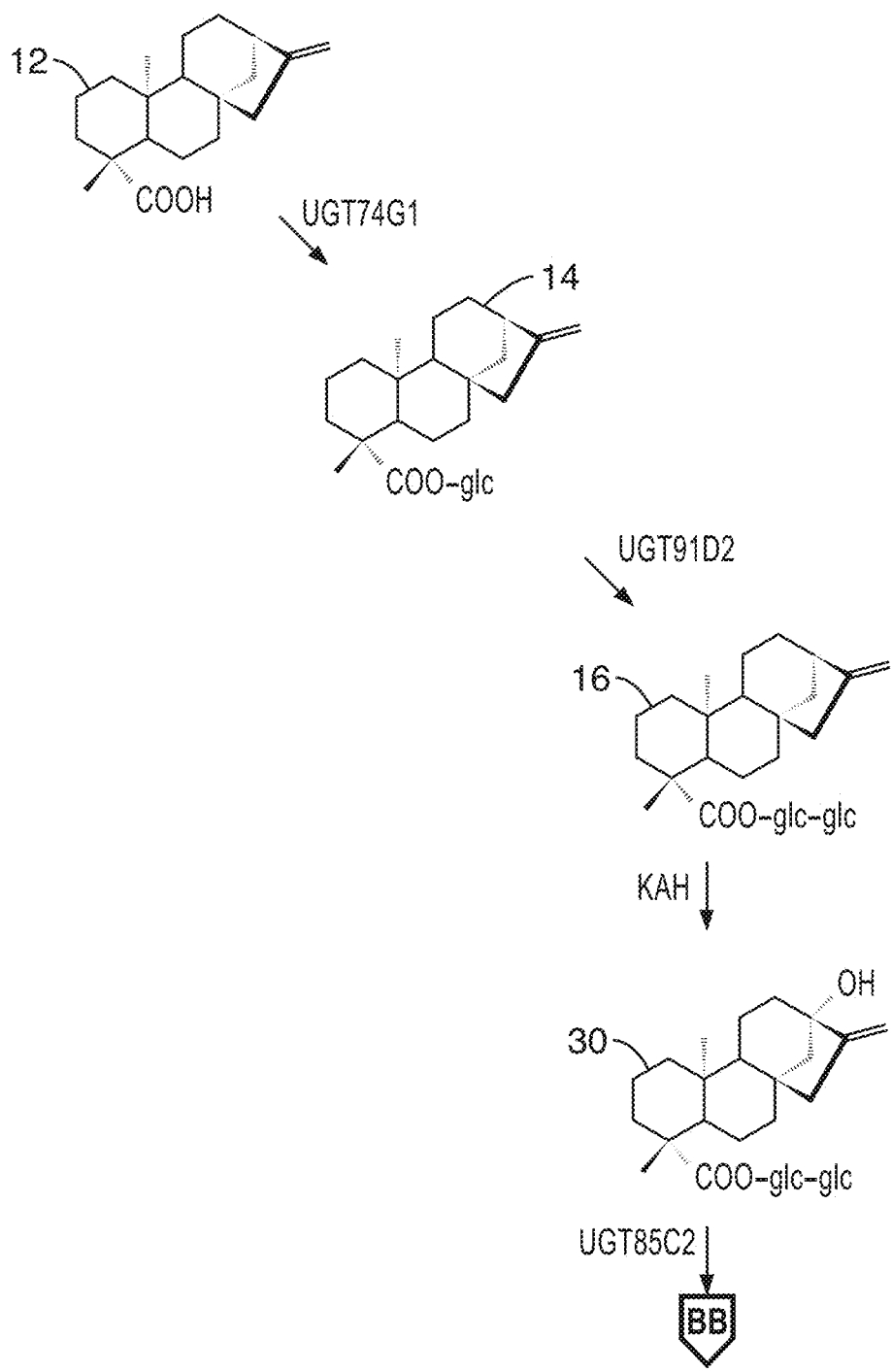
FIG. 3A and FIG. 3B depict a schematic flow diagram of the synthesis of Reb D and/or Reb M from the KA-19-bioside precursor according to another embodiment of the technology.
Figure 3B:
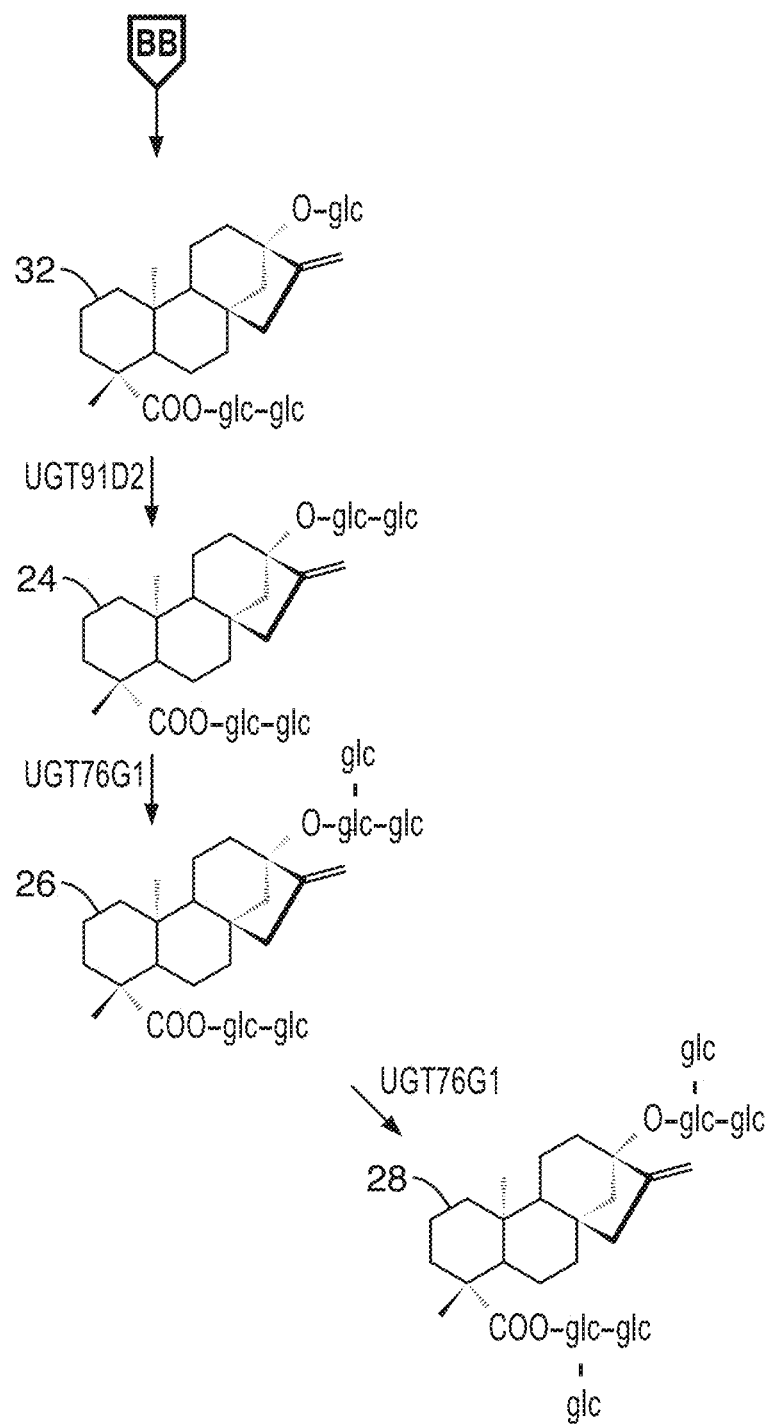

The glycosylation of the primary sugar of the carboxyl group of C-19 of the KA-19-monoside 14 is preferably accomplished with *Stevia* UDP-glucosyltransferase enzyme UGT91D2 (SEQ ID No.: 9) or Os03g0702000 (SEQ ID No: 11) derived from *Oryza sativa* or other enzyme or approach that results in this glycosylation. As illustrated in FIG. 3A and FIG. 3B, the KA-19-bioside precursor 16 can be used in many settings including an alternative biosynthetic route for steviol glycosides Reb E and Reb D. As with the glycosylation forming the KA-19-monoside 14, any suitable sugar and sugar donor can be used to form the KA-19-bioside 16 precursor in the alternative to glucose.

Figure 4A:
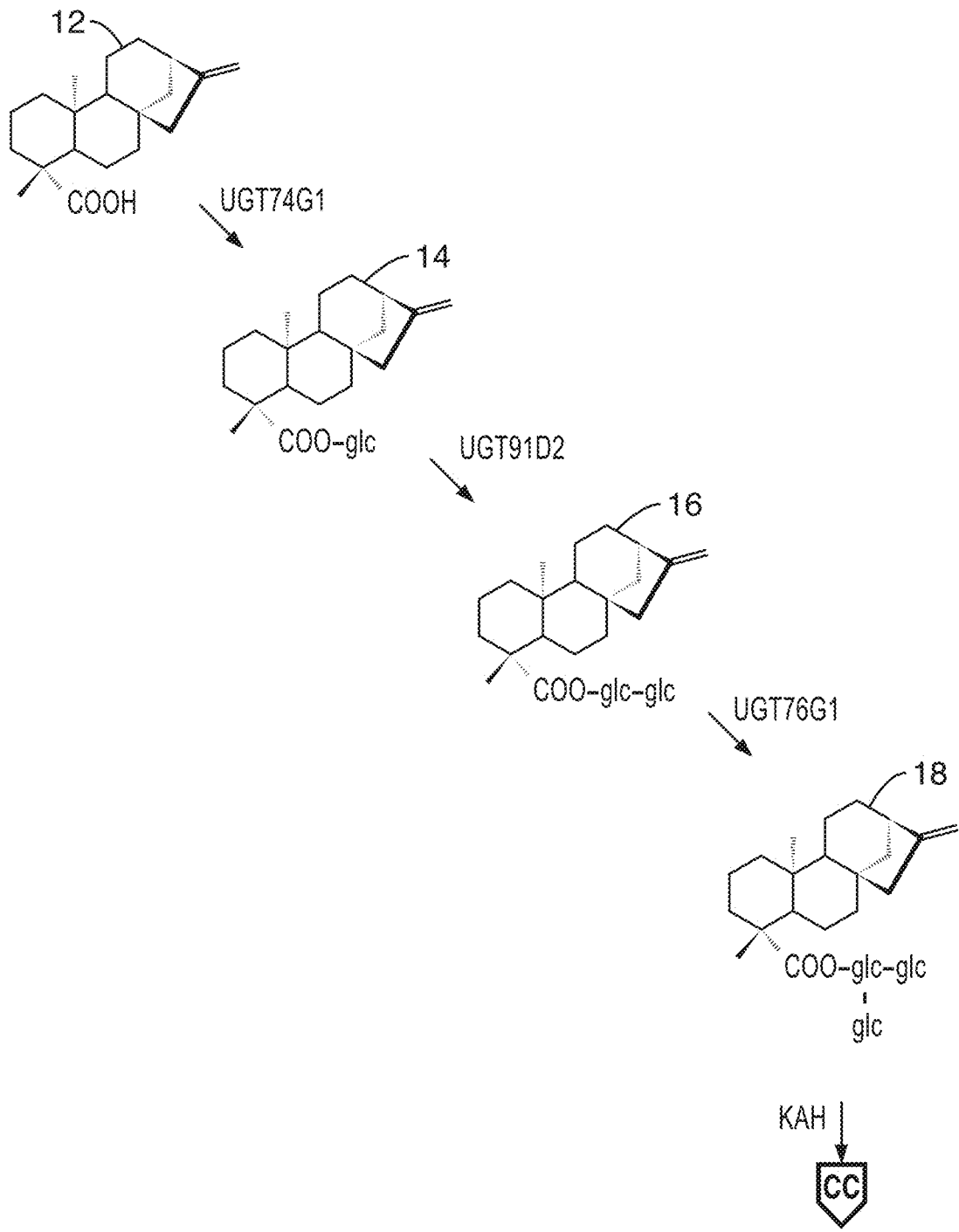
FIG. 4A and FIG. 4B depict a schematic flow diagram of the synthesis of Reb M from the KA-19-trioside precursor according to another embodiment of the technology.
Figure 4B:
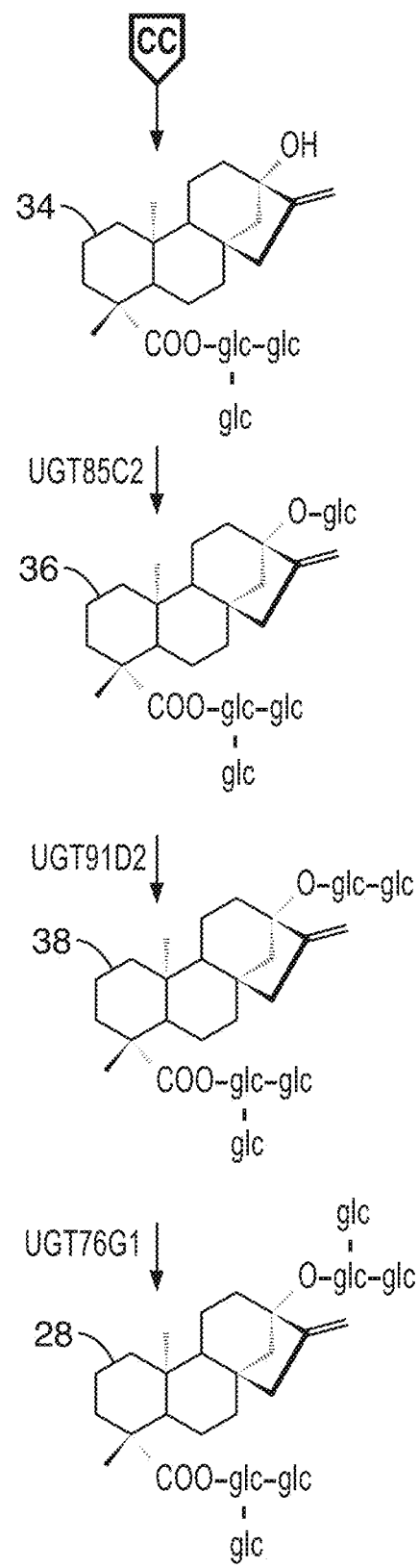

Production of the KA-19-trioside 18 precursor is preferably through a second glycosylation of the primary sugar of C-19 of the KA-19-bioside 16. This glycosylation of the KA-19-bioside 16 to produce the KA-19-trioside 18 precursor is preferably performed by *Stevia* UDP-glucosyltransferase enzyme UGT76G1 (SEQ ID No.: 5) or a functional equivalent. As illustrated in FIG. 4A and FIG. 4B, the KA-19-trioside precursor 18 can be used in many settings including an alternative biosynthetic route for steviol glycosides Reb M.

Furthermore, the individual synthesis pathways from each of the precursors can also be combined in some settings. For example, in the illustration shown in FIG. 5A and FIG. 5B, the KA-19-bioside and KA-19-trioside precursors are combined and the sequential synthesis steps are performed simultaneously and in parallel. Accordingly, the final sweetener composition will include Reb E, Reb D and Reb M in this illustration. The final composition does not require Reb B or Reb A as intermediates as found in the traditional synthesis schemes. Rather than be consumed, the traditional Reb B or Reb A intermediates can become part of the final composition in some embodiments. In addition, the parallel pathways using the KA-19-bioside and KA-19-trioside precursors can be used to increase the yield and exclusively produce Reb M.

Figure 6:
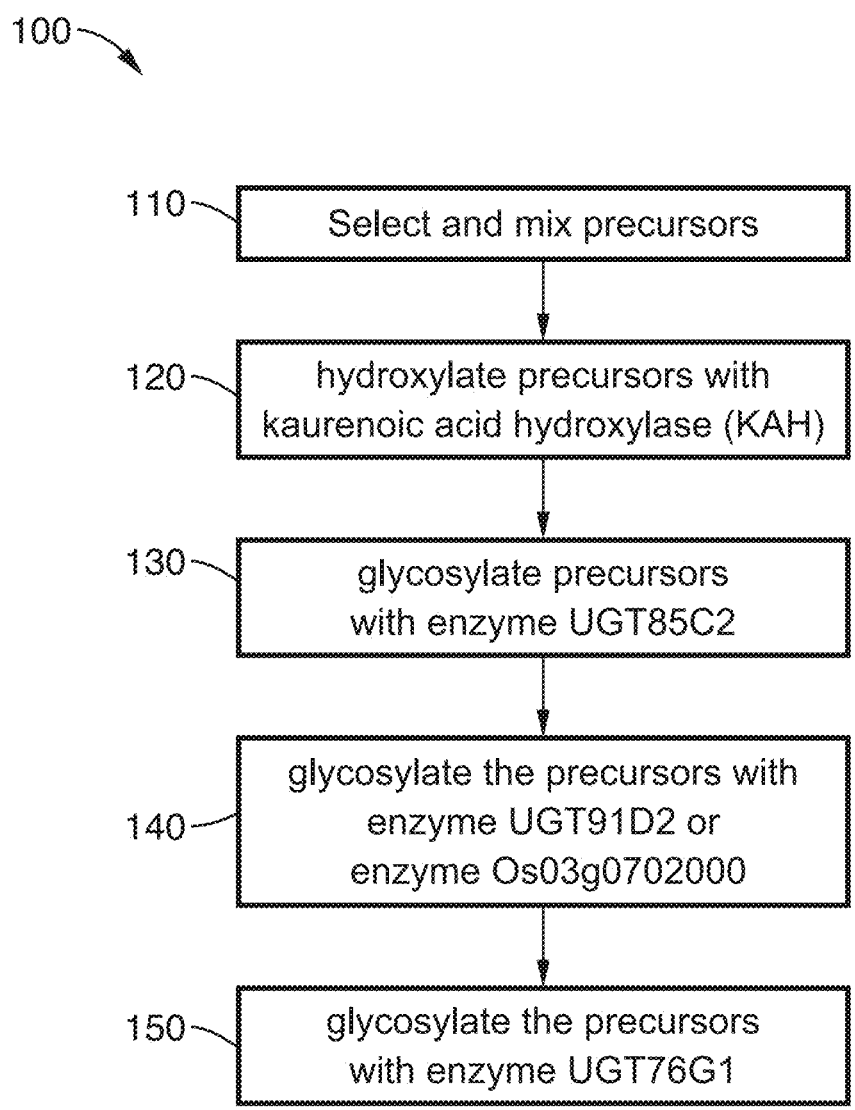
FIG. 6 is a schematic flow diagram of the synthesis of *Stevia* glycosides from a mixture of KA, KA-19-monoside, KA-19-bioside and KA-19-trioside precursors.

The parallel processing of each of the pathways also allows control over the final compositions by mixing different amounts of all or some of the precursors as well as ent-kaurenoic acid 12 as starting materials as shown in FIG. 6. In one embodiment, the natural pathways can also be processed in parallel with the precursor pathways.

Turning now to FIG. 2A and FIG. 2B, one use of the KA-19-monoside precursor 14 in the production of the Reb A glycoside 22 that can be further processed to produce the Reb D glycoside 26 and Reb M glycoside 28 is shown. The synthesis pathway begins with providing the KA-19-monoside precursor 14 from any source. The C13 of the KA-19-monoside 14 is hydroxylated to produce a Steviol-19-monoside 16. In the embodiment shown in FIG. 2A, the hydroxylation is provided by a kaurenoic acid hydroxylase (KAH) or a functional equivalent.

The C13 hydroxyl of the Steviol-19-monoside 16 molecules is then glycosylated to produce Rubusoside 18 molecules. This glycosylation can be performed by *Stevia* UDP-glucosyltransferase enzyme UGT85C2 (SEQ ID No.: 7) or a functional equivalent.

The Rubusoside 18 molecules can be glycosylated with a (2-1) secondary glycosylation to produce Stevioside 20 molecules. This glycosylation of the C13 primary sugar can be accomplished with a *Stevia* UDP-glucosyltransferase enzyme UGT91D2 (SEQ ID No.: 9) or Os03g0702000 (SEQ ID No: 11) or a functional equivalent.

Reb A is produced by glycosylating the C13 primary sugar of the Stevioside 20 molecules with a (3-1) glycosylation to produce Rebaudioside A. A *Stevia* UDP-glucosyltransferase enzyme UGT76G1 (SEQ ID No.: 5) or a functional equivalent can be used to produce the tertiary glycosylation.

FIG. 2B also indicates some additional rebaudioside end products that can be produced with this pathway or Reb A. Rebaudioside E molecules 24 can be produced with a secondary glycosylation of the C19 primary sugar of the Stevioside 20 intermediate using the *Stevia* UDP-glucosyltransferase enzyme UGT91D2 (SEQ ID No.: 9) or Os03g0702000 (SEQ ID No.: 11) or a functional equivalent.

In addition, Reb D molecules 26 can be produced with a C13 tertiary glycosylation of Reb E using *Stevia* UDP-glucosyltransferase enzyme UGT76G1 (SEQ ID No.: 5) or a functional equivalent.

Reb D can also be produced with a secondary glycosylation of the C19 primary sugar of the Reb A 22 intermediate using the *Stevia* UDP-glucosyltransferase enzyme UGT91D2 (SEQ ID No.: 9) or Os03g0702000 (SEQ ID No.: 11) or a functional equivalent.

Also shown in FIG. 2B is the conversion of Reb D molecules 26 to Reb M molecules 28 using *Stevia* UDP enzyme UGT76G1 (SEQ ID No.: 5) or a functional equivalent.

The KA-19-bioside precursor 16 can also be used to produce Reb D 26 and Reb M 28 steviol glycosides as illustrated in FIG. 3A and FIG. 3B. The C13 of the prepared KA-19-bioside precursor 16 is hydroxylated to produce a Steviol-19-bioside 30. The hydroxylation is preferably provided by a kaurenoic acid hydroxylase (KAH) or a functional equivalent.

The C13 hydroxyl of the Steviol-19-bioside 30 is then glycosylated to produce steviol-13-mono-19-bioside molecules 32, preferably with the *Stevia* UDP-glucosyltransferase enzyme UGT85C2 (SEQ ID No.: 7) or a functional equivalent.

The C13 primary sugar of the Steviol-13-mono-19-bioside 32 molecules are glycosylated to produce Rebaudioside E 24 molecules with a *Stevia* UDP-glucosyltransferase enzyme UGT91D2 (SEQ ID No.: 9) or Os03g0702000 (SEQ ID No.: 11) or a functional equivalent.

The Reb E molecules 24 alone can be isolated and purified or they can provide a substrate for further processing to produce Reb D molecules 26 or Reb M molecules 28 with a *Stevia* UDP enzyme UGT76G1 (SEQ ID No.: 5) or a functional equivalent.

FIG. 4A and FIG. 4B illustrate one use of the KA-19-trioside precursor to produce primarily Rebaudioside M molecules 28. In the pathway embodiment beginning in FIG. 4A, the C13 of the KA-19-tri-glycoside precursor is hydroxylated to produce steviol-19-trioside 34, preferably using a kaurenoic acid hydroxylase (KAH) or a functional equivalent.

The C13 hydroxyl of the steviol-19-trioside 34 molecules is then glycosylated to produce steviol-13-mono-19-trioside 36 molecules, preferably with a *Stevia* UDP-glucosyltransferase enzyme UGT85C2 (SEQ ID No.: 7) or a functional equivalent.

The C13 primary sugar of the Steviol-13-mono-19-trioside 36 molecules are glycosylated to produce steviol-13-bio-19-trioside 38. The secondary glycosylation can be performed with a *Stevia* UDP-glucosyltransferase enzyme UGT91D2 (SEQ ID No.: 9) or Os03g0702000 (SEQ ID No.: 11) or a functional equivalent.

Finally, the C13 primary sugar of the steviol-13-bio-19-trioside 38 molecules is glycosylated with a (3-1) glycosylation to produce Rebaudioside M molecules 28. This glycosylation can be performed with a *Stevia* UDP enzyme UGT76G1 (SEQ ID No.: 5) or a functional equivalent.

Figure 5A:
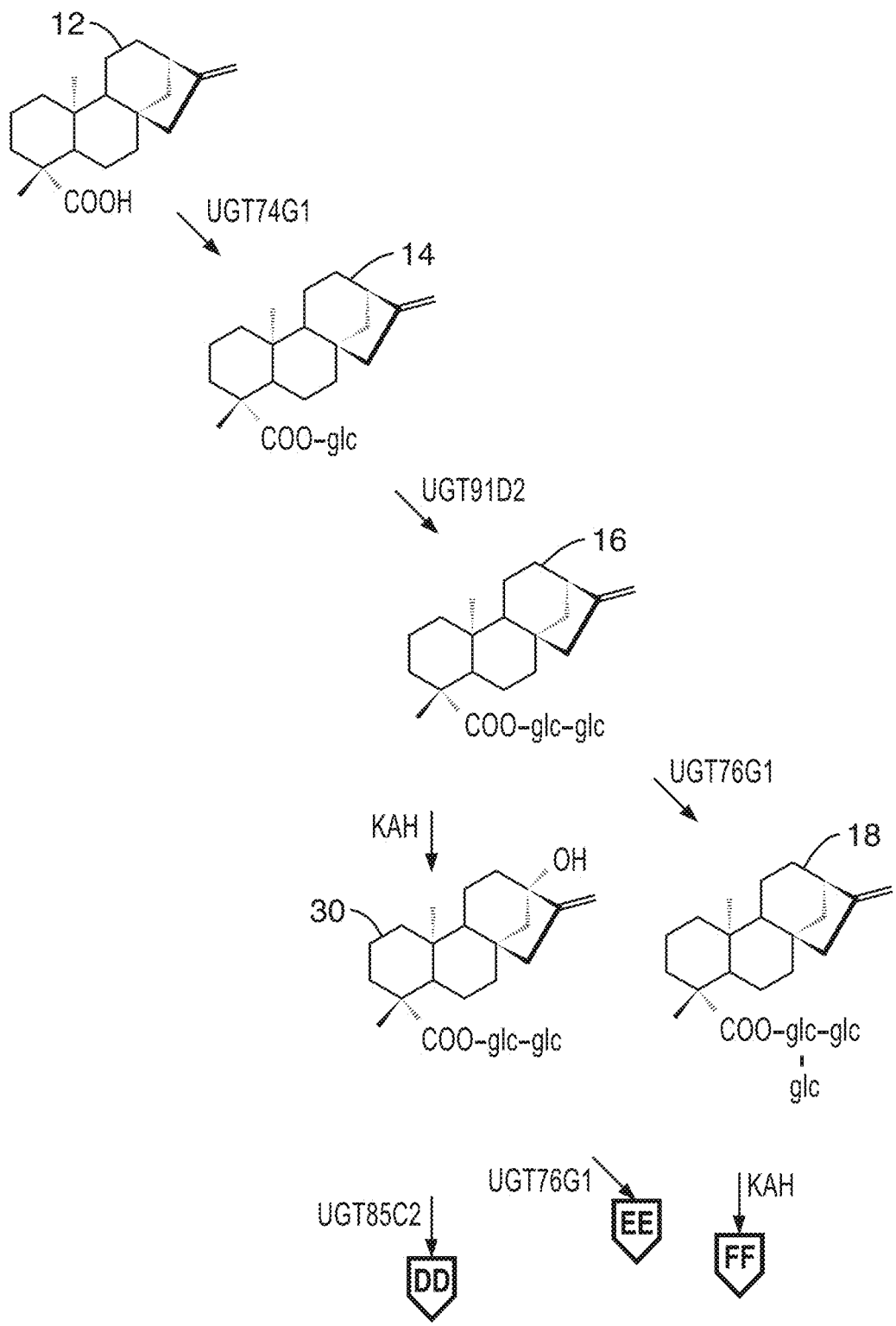
FIG. 5A and FIG. 5B depict a schematic flow diagram of the synthesis of Reb D and Reb M from the simultaneous synthesis of a mixture of KA-19-bioside and KA-19-trioside precursors according to another embodiment of the technology.
Figure 5B:
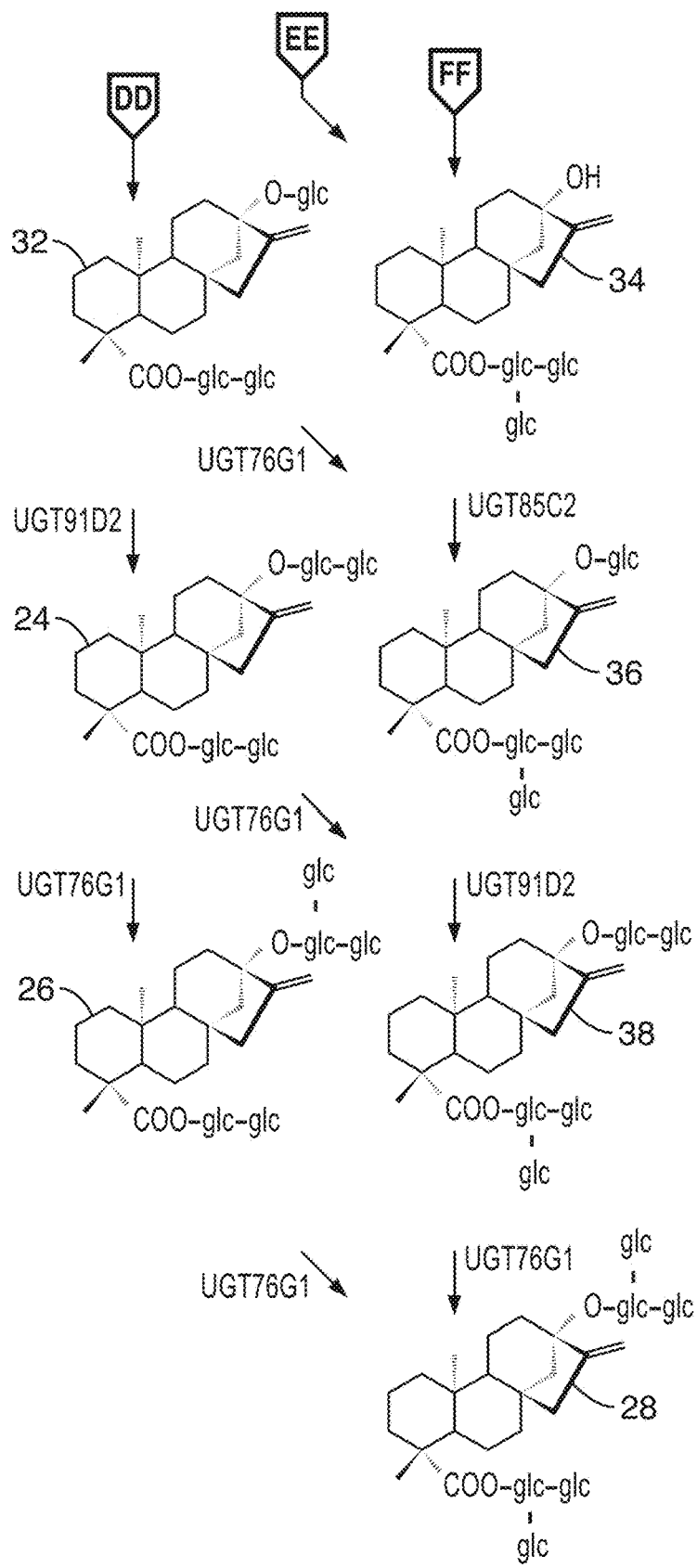

It can be seen that the pathways of ent-kaurenoic acid 12 and the KA-19-monoside 14, KA-19-bioside 16 and KA-19-trioside 18 precursors can be conducted in parallel. For example, the pathways of KA-19-bioside 16 and KA-19-trioside 18 precursors can be synchronized and conducted in parallel as shown in FIG. 5A and FIG. 5B. Mixed KA-19-bioside 16 and KA-19-trioside 18 precursors can be exposed to the same sequence of enzymes. In the embodiment shown in FIG. 5A and FIG. 5B the sequence of KAH, UGT85C2, UGT91D2 and UGT76G1 can produce results in parallel.

In addition, the introduction of UGT76G1 will produce a shift from the KA-19-bioside 16 pathway to the KA-19-trioside 18 pathway in this scheme. For example, the Steviol-13-mono-19-bioside 32 from the KA-19-bioside pathway can be converted to Steviol-13-mono-19-trioside 36 of the KA-19-trioside 18 pathway. Likewise, the introduction of UGT91D2 will produce a shift from the KA-19-bioside 16 pathway to the KA-19-bioside 18 pathway.

Similar synchronized pathway combinations can be assembled. For example, the KA-19-monoside 14 pathway can be paired with the KA-19-bioside 16 or KA-19-trioside 18 pathways. Likewise the ent-kaurenoic acid 12 pathway can be matched with one or more of the precursor pathways.

Referring now to FIG. 6, a method 100 for synthesis of selected Steviol glycosides with KA-glycoside precursors is described. At block 110, the individual or mixture of KA-19-monoside 14, KA-19-bioside 16, KA-19-trioside 18 precursors or ent-kaurenoic acid 12 is selected. The parallel pathway processing permits control over the composition of the final product or products with the selection of a type of precursor and its associated pathway and products. The relative quantities of particular end products that are produced can also be emphasized and controlled through the amount of one precursor that is used in comparison to the others that are used.

At block 120 the precursor mixture or precursor/ent-kaurenoic acid mixture is hydroxylated. In the embodiment of FIG. 6, the hydroxylase is kaurenoic acid hydroxylase (KAH) is used. However, any hydroxylase that will form a C13 hydroxyl of the precursors can be used.

The C13 hydroxylated precursor mixture or precursor/ent-kaurenoic acid mixture is then glycosylated at block 130 with *Stevia* UDP-glucosyltransferase enzyme UGT85C2 (SEQ ID No.: 7) or a functional equivalent. In one embodiment, Steviol is added to the mix prior to the first glycosylation.

At block 140, the C13 primary sugar is glycosylated with a secondary sugar with a *Stevia* UDP-glucosyltransferase enzyme UGT91D2 (SEQ ID No.: 9) or Os03g0702000 (SEQ ID No.: 11) or a functional equivalent.

Finally, at block 150 of FIG. 6, the C13 sugar of the precursor mixture is glycosylated with a tertiary sugar with a *Stevia* UDP-glucosyltransferase enzyme UGT76G1 (SEQ ID No.: 5) or a functional equivalent.

The resulting steviol glycosides can be isolated and concentrated or can be the substrate for further processing.

The technology may be better understood with reference to the accompanying examples, which are intended for purposes of illustration only and should not be construed as in any sense limiting the scope of the claims appended hereto.

Example 1

In order to demonstrate the functionality of the synthesis schemes, several different glucosyltransferase gene and protein expression constructs were obtained from *Stevia rebudiana*. Amino acid (SEQ ID: 1) and nucleotide (SEQ ID: 2) sequences for UGT74G1 were obtained from the National Center for Biotechnology Information (NCBI). Primers were designed for UGT74G1 (SEQ ID: 13 and 14) using PrimerQuest (IDT) with additional homology for ligation independent cloning into pLATE-51 (Thermo). Sequences for UGT74G1 and the other UGTs used for isolation and cloning of glucosyltransferases from *Stevia rebudiana* are listed in Table 1.

To clone the UGT coding sequences from *Stevia*, mRNA was extracted from greenhouse grown *Stevia* plants of varying ages and extracted using the Spectrum Plant Total RNA Kit (Sigma-Aldrich). The mRNA was reverse-transcribed into single stranded DNA with the Omniscript Reverse Transcription kit and Oligo dT primers (Qiagen). UGT74G1 was amplified from the resulting *Stevia* cDNA using oligonucleotide primers (SEQ ID: 13 and 14) with Phusion DNA polymerase (New England Biolabs).

Gene products were separated by gel electrophoresis, excised and purified using a Qiaquick DNA gel extraction kit (Qiagen). Gene products were then inserted in pLATE-51 vector using the aLlCator LIC Cloning and Expression Kit 2 (Thermo). Transformants were selected on media containing ampicillin and verified by sequence. The resulting plasmid contained the UGT74G1 coding sequence with an N-terminal 6× histidine tag under the control of the lactose-inducible promoter (SEQ ID: 3 and 4). The UGT74G1 plasmid was transformed into *E. coli* BL21-DE3 cells and grown at 20° C. with 220 rpm shaking until an OD600 of 0.6 was reached, at which time the culture was induced with 1 mM IPTG. After 24 hours of induction the UGT74G1 protein was extracted from the cells using Bacterial Protein Extraction Reagent (BPER), (Thermo). Induction was verified by polyacrylamide gel electrophoresis and coomassie staining with GelCode-Blue (Pierce). The remaining UGTs from *Stevia* were cloned in the same way with their specific sequences and primers (Table 1). Os03g0702000 (SEQ ID No.: 12) was synthesized in two fragments, and assembled into a proprietary plasmid backbone for shuttling. This plasmid product was used for PCR with oligonucleotide primers (SEQ ID: 21 and 22) and inserted into pLATE-51 as described above.

Example 2

The production of the KA-19-monoside precursor (19-O-β-D-glucose-kaurenoic acid) from kaurenoic acid was demonstrated with *Stevia* UGT enzymes. KA was reacted with UGT enzymes from *Stevia* known to participate in the steviol glycoside biosynthesis.

The production of KA-19-monoside was seen only in the reactions incubated with UGT74G1 (SEQ ID No.: 1)

extracts and was dependent on the inclusion of UDPG to the reaction. No other UGT enzymes tested showed any activity towards primary glycosylation of KA at the C19 carboxyl group.

Kaurenoic acid (KA) conversion assays were performed in 50 mM $KPO_4$, pH 7.2, 2 mM $MgCl_2$, 10 μl/ml BSA, 50 uM ent-kaurenoic acid, 1 mM uridine-diphospho-glucose (UDPG), and 10% induced bacterial lysate or purified protein. The reaction was incubated at 30° C. for 12 hours with shaking at 220 rpm. Reactions were stopped by adding 80% acetonitrile, vortexed 5', and centrifuged at 13,000 rpm for 10'. The resulting reaction supernatants were observed by separation on a mixed-mode wax-1 column (Thermo) with an isocratic elution of 80:20 acetonitrile:ammonium formate 10 mM, pH 6.0 on an UHPLC system equipped with a diode array detector (Thermo).

HPLC chromatograms from the UGT assays were also acquired. The results showed that reactions that contain UGT76G1 did not consume any of the KA (8.3 minutes) in the reaction. Whereas UGT74G1 (SEQ ID No.: 1) caused the depletion of the KA and the formation of the KA-19-monoside (2.8 minutes). A peak area of 7.390 mAU*min was observed for the KA-19-monoside produced from the glycosylation reaction. In addition, glycosylation of the carboxyl C19 group of steviol glycosides increases the hydrophobicity of the molecule, resulting in the accelerated elution of C19 glycosylated steviol glycosides with HILIC separation. The elution time of KA-19-monoside was accelerated relative to KA (2.8' vs 8.3', respectively), consistent with glycosylation at the C19 carboxyl group. Additionally, spectral scans of isolated product reveal conservation of the diterpenoid backbone of KA-19-monoside.

Accordingly, only SrUGT74G1 (SEQ ID No.: 1) was seen to be capable of converting KA to the KA-19-monoside. The SrUGT76G1 (SEQ ID No.: 5) and SrUGT85C2 (SEQ ID No.: 7) enzymes showed no activity towards KA, but their activity was confirmed against Stevioside and steviol, respectively. Taken together, these results show that the UGT74G1 glucosyltransferase is responsible for conversion of KA to KA-19-monoside, indicating a previously unknown activity for UGT74G1.

Example 3

Production of the KA-19-bioside and KA-19-trioside precursors from the KA-19-monoside was also demonstrated. KA conversion assays were performed as described in Example 2 with analysis carried out with 80:20 acetonitrile: ammonium formate 10 mM, pH 3.0 used as the solvent. Accordingly, reaction of 10% v/v SrUGT74G1 (SEQ ID No.: 1) with KA resulted in the production of KA-19-monoside.

Upon addition of Os03g0702000 (SEQ ID No.: 11) to the SrUGT74G1+KA reaction, the KA-19-monoside was efficiently converted to the KA-19-bioside. Os03g0702000 was added at 10% v/v to the SrUGT74G1+KA reaction and a reaction product was formed that was shown to be UDPG-dependent.

Upon further addition of SrUGT76G1 (SEQ ID No.: 5) to the Os03g0702000+SrUGT74G1+KA reaction, the KA-19-Bioside was converted to the KA-19-trioside. SrUGT76G1 was added at 10% v/v to the SrUGT74G1+Os03g0702000+ KA reaction and the resulting KA-19-trioside that was formed was also UDPG-dependent.

Addition of SrUGT76G1 to the SrUGT74G1+KA reaction did not yield any products. Incubations that lacked UDPG did not convert any KA to the KA-glycosides.

KA and KA-glycosides have similar absorbance patterns that could be seen in spectrophotometric spectral scans.

KA-19-trioside also demonstrated significantly decreased hydrophobicity compared to KA, KA-19-monoside, and the KA-19-bioside precursors. It is likely that additional glycosylations would further improve the solubility of KA-19-trioside.

From the description herein, it will be appreciated that the present disclosure encompasses multiple embodiments which include, but are not limited to, the following:

1. A method of producing kaureonic acid precursors, comprising (a) providing a source of ent-kaurenoic acid; and (b) glycosylating C19 carboxyl groups of the kaurenoic acid molecules to produce molecules of kaurenoic-acid-19-monoglycoside.

2. The method of any previous embodiment, wherein the glycosylation of C19 carboxyl groups of kaurenoic acid is produced with enzyme UGT74G1 (SEQ ID No: 1).

3. The method of any previous embodiment, wherein the glycosylation of C19 carboxyl groups of kaurenoic acid is produced with a cyclodextrin glucanotransferase.

4. The method of any previous embodiment, wherein the glycosylation step comprises attaching a sugar selected from the group of sugars consisting of fructose, glucose, xylose, and rhamnose.

5. The method of any previous embodiment, wherein the KA-19-monoside precursor is used to produce Rebaudioside A, the method comprising: hydroxylating the C13 of the KA-19-monoside to produce Steviol-19-monoside; glycosylating the C13 hydroxyl of the Steviol-19-monoside molecules with a primary sugar to produce rubusoside molecules; glycosylating the primary sugar with a secondary sugar on the rubusoside molecules with a (2-1) glycosylation to produce Stevioside molecules; and glycosylating Stevioside molecules with a (3-1) glycosylation with a second secondary sugar to produce Rebaudioside A.

6. The method of any previous embodiment, wherein the hydroxylation of the C13 carbon of the KA-19-monoside is produced with kaurenoic acid hydroxylase (KAH).

7. The method of any previous embodiment, wherein the glycosylation of the C13 hydroxyl of the Steviol-19-monoside molecules is produced with the enzyme UGT85C2 (SEQ ID No.: 7)

8. The method of any previous embodiment, wherein the glycosylation of Rubusoside is produced with the enzyme UGT91D2 (SEQ ID No.: 9).

9. The method of any previous embodiment wherein the glycosylation of Stevioside is produced with the enzyme UGT76G1 (SEQ ID NO.: 5).

10. A method of producing glycosides from kaureonic acid precursors, comprising: (a) providing a source of ent-kaurenoic acid; (b) glycosylating C19 carboxyl groups of the kaurenoic acid molecule with a primary sugar to produce molecules of kaurenoic-acid-19-monoglycoside; and (c) glycosylating the C19 primary sugar of the kaurenoic-acid-19-monoglycoside to produce kaurenoic-acid-19-bi-glycoside (KA-19-(2-1)-bioside precursor).

11. The method of any previous embodiment, wherein the glycosylation of C19 carboxyl groups of kaurenoic acid is produced with enzyme UGT74G1 (SEQ ID No.: 1) or a cyclodextrin glucanotransferase.

12. The method of any previous embodiment, wherein the glycosylation steps comprise attaching a sugar selected from the group of sugars consisting of fructose, glucose, xylose, and rhamnose.

13. The method of any previous embodiment wherein the glycosylation of C19 primary sugar of kaurenoic-acidmonoglycoside to attach a secondary sugar is produced with enzyme UGT91D2 (SEQ ID NO.: 9) or Os03g0702000 (SEQ ID NO.: 11).

14. The method of any previous embodiment wherein the KA-19-(2-1)-bioside precursor is used to produce Rebaudioside E, the method comprising: hydroxylating the C13 of the KA-19-(2-1)-bioside to produce steviol-19-bioside; glycosylating the C13 hydroxyl of the steviol-19 bioside molecules with a primary sugar to produce steviol-13-mono-19-bioside molecules; and glycosylating the C13 primary sugar of steviol-13 mono-19-bioside molecules to produce Rebaudioside E molecules.

15. The method of any previous embodiment further comprising: glycosylating the C13 primary sugar of Rebaudioside E molecules with a (3-1) glycosylation to produce Rebaudioside D molecules.

16. The method of any previous embodiment further comprising: glycosylating Rebaudioside D molecules with a (3-1) glycosylation of the primary sugar at C19 to produce Rebaudioside M molecules.

17. The method of any previous embodiment wherein the glycosylation of Rebaudioside D molecules is produced with enzyme UGT76G1 (SEQ ID NO.: 5).

18. The method of any previous embodiment wherein the hydroxylation of the C13 carbon of the KA-19-(2-1)-bioside precursor is produced with kaurenoic acid hydroxylase (KAH).

19. The method of any previous embodiment wherein the glycosylation of the C13 hydroxyl of the steviol-19-bioside molecules is produced with the enzyme UGT85C2 (SEQ ID No.: 7).

20. The method of any previous embodiment wherein the glycosylation of steviol-13-mono-19-bioside is produced with the enzyme UGT91D2 (SEQ ID No.: 9).

21. The method of any previous embodiment wherein the glycosylation of Rebaudioside E is produced with the enzyme UGT76G1 (SEQ ID No.: 5).

22. A method of producing glycosides from kaurenoic acid precursors, comprising: (a) providing a source of ent-kaurenoic acid; (b) glycosylating C19 carboxyl groups of the kaurenoic acid molecules with a primary sugar to produce molecules of kaurenoic-acid-19-monoglycoside; and (c) glycosylating C19 primary sugars of the kaurenoic-acid-19-monoglycoside to produce a kaurenoic-acid-19-bioside; (d) glycosylating C19 primary sugars of the kaurenoic-acid-19-bi-glycoside to produce kaurenoic-acid-19-tri-glycoside (KA-19-trioside precursor).

23. The method of any previous embodiment wherein the glycosylation of C19 carboxyl groups of kaurenoic acid is produced with enzyme SrUGT74G1 (SEQ ID No.: 1) or a cyclodextrin glucanotransferase.

24. The method of any previous embodiment, wherein the glycosylation steps comprise attaching a sugar selected from the group of sugars consisting of fructose, glucose, xylose, and rhamnose.

25. The method of any previous embodiment, wherein the KA-19-tri-glycoside precursor is used to produce Rebaudioside M, the method comprising: hydroxylating the C13 of the KA-19-trioside precursor to produce steviol-19-trioside; glycosylating the C13 hydroxyl of the steviol-19-trioside molecules to produce steviol-13-mono-19-trioside molecules; glycosylating steviol-13-mono-19-trioside molecules to produce steviol-13-bio-19-trioside; and glycosylating the C13 hydroxyl of the steviol-13-bio-19-trioside molecules with a (3-1) glycosylation to produce Rebaudioside M molecules.

26. The method of any previous embodiment, wherein the hydroxylation of the C13 carbon of the KA-19-trioside precursor is produced with kaurenoic acid hydroxylase (KAH).

27. The method of any previous embodiment, wherein the glycosylation of the C13 hydroxyl of the steviol-19-trioside molecules is produced with the enzyme UGT85C2 (SEQ ID No.: 7)

28. The method of any previous embodiment, wherein the glycosylation of steviol-13-mono-19-trioside is produced with the enzyme UGT91D2 (SEQ ID No.: 9).

29. The method of any previous embodiment wherein the glycosylation of steviol-13-bio-19-trioside is produced with the enzyme UGT76G1 (SEQ ID No.: 5).

30. A method of producing a mixture of steviol glycosides from kaurenoic acid precursors, comprising: (a) mixing one or more kaurenoic-acid-19-monoglycoside, kaurenoic-acid-19-bi-glycoside, and kaurenoic-acid-19-tri-glycoside precursors; (b) hydroxylating the mixture of precursors with kaurenoic acid hydroxylase (KAH); (c) glycosylating the hydroxylated precursors with enzyme UGT85C2 (SEQ ID No.: 7); (d) glycosylating the precursors with enzyme UGT91D2 (SEQ ID No.: 9) or enzyme Os03g0702000 (SEQ ID No.: 11); and (e) glycosylating the precursors with enzyme UGT76G1 (SEQ ID No.: 5) to produce steviol glycosides corresponding to the type and concentration of precursors that are mixed.

31. The method of any previous embodiment, further comprising: adding ent-kaurenoic acid to the mixture of precursors; wherein Rebaudioside B will be produced and present in the steviol glycosides that are produced.

32. The method of any previous embodiment, further comprising: selecting a rebaudioside composition to be produced; selecting an ent-kaurenoic acid precursor that will produce each selected rebaudioside; and providing the selected ent-kaurenoic acid precursors in stoichiometric amounts to produce the selected composition.

33. A biosynthetic precursor comprising kaurenoic-acid-19-monoside.

34. A biosynthetic precursor comprising kaurenoic-acid-19-bioside.

35. A biosynthetic precursor comprising kaurenoic-acid-19-trioside.

Although the description herein contains many details, these should not be construed as limiting the scope of the disclosure but as merely providing illustrations of some of the presently preferred embodiments. Therefore, it will be appreciated that the scope of the disclosure fully encompasses other embodiments which may become obvious to those skilled in the art.

In the claims, reference to an element in the singular is not intended to mean "one and only one" unless explicitly so stated, but rather "one or more." All structural, chemical, and functional equivalents to the elements of the disclosed embodiments that are known to those of ordinary skill in the art are expressly incorporated herein by reference and are intended to be encompassed by the present claims. Furthermore, no element, component, or method step in the present disclosure is intended to be dedicated to the public regardless of whether the element, component, or method step is explicitly recited in the claims. No claim element herein is to be construed as a "means plus function" element unless the element is expressly recited using the phrase "means for". No claim element herein is to be construed as a "step plus function" element unless the element is expressly recited using the phrase "step for".

TABLE 1

| Enzyme | DNA sequence | AA sequence | 5' Cloning Primer | 3' Cloning Primer |
|---|---|---|---|---|
| UGT74G1 | Seq 2 | Seq 1 | Seq 13 | Seq 14 |
| UGT74G1-his | Seq 4 | Seq 3 | | |
| UGT76G1 | Seq 6 | Seq 5 | Seq 15 | Seq 16 |
| UGT85C2 | Seq 8 | Seq 7 | Seq 17 | Seq 18 |

TABLE 1-continued

| Enzyme | DNA sequence | AA sequence | 5' Cloning Primer | 3' Cloning Primer |
|---|---|---|---|---|
| UGT91D2 | Seq 10 | Seq 9 | Seq 19 | Seq 20 |
| Os03g0702000 | Seq 12 | Seq 11 | Seq 21 | Seq 22 |

What is claimed is:

1. A kaurenoic-acid-19-monoglycoside having the following structural formula:

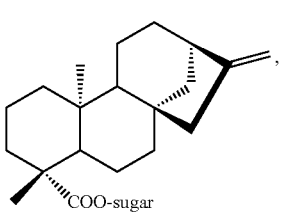

wherein the sugar is fructose.

2. A kaurenoic-acid-19-bi-glycoside having the following structural formula:

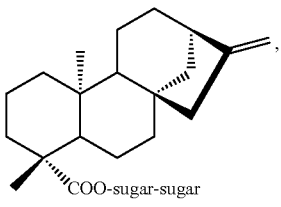

wherein the sugar is selected from the group consisting of glucose, fructose, xylose and rhamnose, with the proviso that COO-sugar-sugar is other than COO-glucose-glucose.

3. A kaurenoic-acid-19-tri-glycoside having the following structural formula:

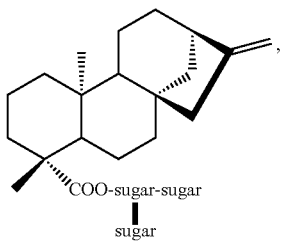

wherein the sugar is selected from the group consisting of glucose, fructose, xylose and rhamnose.

4. The compound of claim 2, wherein the sugar comprises a glucose.

5. The compound of claim 2, wherein the sugar comprises a fructose.

6. The compound of claim 2, wherein the sugar comprises a xylose.

7. The compound of claim 2, wherein the sugar comprises a rhamnose.

8. The compound of claim 3, wherein the sugar comprises a glucose.

9. The compound of claim 3, wherein the sugar comprises a fructose.

10. The compound of claim 3, wherein the sugar comprises a xylose.

11. The compound of claim 3, wherein the sugar comprises a rhamnose.

* * * * *

SEQUENCE LISTING

<160> NUMBER OF SEQ ID NOS: 22

<210> SEQ ID NO 1
<211> LENGTH: 460
<212> TYPE: PRT
<213> ORGANISM: Stevia rebaudiana

<400> SEQUENCE: 1

```
Met Ala Glu Gln Gln Lys Ile Lys Lys Ser Pro His Val Leu Leu Ile
1               5                   10                  15

Pro Phe Pro Leu Gln Gly His Ile Asn Pro Phe Ile Gln Phe Gly Lys
            20                  25                  30

Arg Leu Ile Ser Lys Gly Val Lys Thr Thr Leu Val Thr Thr Ile His
        35                  40                  45

Thr Leu Asn Ser Thr Leu Asn His Ser Asn Thr Thr Thr Thr Ser Ile
    50                  55                  60

Glu Ile Gln Ala Ile Ser Asp Gly Cys Asp Glu Gly Gly Phe Met Ser
65                  70                  75                  80

Ala Gly Glu Ser Tyr Leu Glu Thr Phe Lys Gln Val Gly Ser Lys Ser
                85                  90                  95

Leu Ala Asp Leu Ile Lys Lys Leu Gln Ser Glu Gly Thr Thr Ile Asp
            100                 105                 110

Ala Ile Ile Tyr Asp Ser Met Thr Glu Trp Val Leu Asp Val Ala Ile
        115                 120                 125

Glu Phe Gly Ile Asp Gly Gly Ser Phe Phe Thr Gln Ala Cys Val Val
    130                 135                 140

Asn Ser Leu Tyr Tyr His Val His Lys Gly Leu Ile Ser Leu Pro Leu
145                 150                 155                 160

Gly Glu Thr Val Ser Val Pro Gly Phe Pro Val Leu Gln Arg Trp Glu
                165                 170                 175

Thr Pro Leu Ile Leu Gln Asn His Glu Gln Ile Gln Ser Pro Trp Ser
            180                 185                 190

Gln Met Leu Phe Gly Gln Phe Ala Asn Ile Asp Gln Ala Arg Trp Val
        195                 200                 205

Phe Thr Asn Ser Phe Tyr Lys Leu Glu Glu Val Ile Glu Trp Thr
    210                 215                 220

Arg Lys Ile Trp Asn Leu Lys Val Ile Gly Pro Thr Leu Pro Ser Met
225                 230                 235                 240

Tyr Leu Asp Lys Arg Leu Asp Asp Asp Lys Asp Asn Gly Phe Asn Leu
                245                 250                 255

Tyr Lys Ala Asn His His Glu Cys Met Asn Trp Leu Asp Asp Lys Pro
            260                 265                 270

Lys Glu Ser Val Val Tyr Val Ala Phe Gly Ser Leu Val Lys His Gly
        275                 280                 285

Pro Glu Gln Val Glu Glu Ile Thr Arg Ala Leu Ile Asp Ser Asp Val
    290                 295                 300
```

```
Asn Phe Leu Trp Val Ile Lys His Lys Glu Glu Gly Lys Leu Pro Glu
305                 310                 315                 320

Asn Leu Ser Glu Val Ile Lys Thr Gly Lys Gly Leu Ile Val Ala Trp
                325                 330                 335

Cys Lys Gln Leu Asp Val Leu Ala His Glu Ser Val Gly Cys Phe Val
                340                 345                 350

Thr His Cys Gly Phe Asn Ser Thr Leu Glu Ala Ile Ser Leu Gly Val
                355                 360                 365

Pro Val Ala Met Pro Gln Phe Ser Asp Gln Thr Thr Asn Ala Lys
370                 375                 380

Leu Leu Asp Glu Ile Leu Gly Val Gly Val Arg Val Lys Ala Asp Glu
385                 390                 395                 400

Asn Gly Ile Val Arg Arg Gly Asn Leu Ala Ser Cys Ile Lys Met Ile
                405                 410                 415

Met Glu Glu Glu Arg Gly Val Ile Ile Arg Lys Asn Ala Val Lys Trp
                420                 425                 430

Lys Asp Leu Ala Lys Val Ala Val His Glu Gly Gly Ser Ser Asp Asn
                435                 440                 445

Asp Ile Val Glu Phe Val Ser Glu Leu Ile Lys Ala
450                 455                 460

<210> SEQ ID NO 2
<211> LENGTH: 1383
<212> TYPE: DNA
<213> ORGANISM: Stevia rebaudiana

<400> SEQUENCE: 2
atggcggaac aacaaaagat caagaaatca ccacacgttc tactcatccc attcccttta        60
caaggccata taaacccttt catccagttt ggcaaacgat taatctccaa aggtgtcaaa       120
acaacacttg ttaccaccat ccacacctta aactcaaccc taaaccacag taacaccacc       180
accacctcca tcgaaatcca agcaatttcc gatggttgtg atgaaggcgg ttttatgagt       240
gcaggagaat catatttgga acattcaaa  caagttgggt ctaaatcact agctgactta       300
atcaagaagc ttcaaagtga aggaaccaca attgatgcaa tcatttatga ttctatgact       360
gaatgggttt tagatgttgc aattgagttt ggaatcgatg tggttcgtt  tttcactcaa       420 gcttgtgttg taaacagctt atattatcat gttcataagg gtttgatttc tttgccattg       480
ggtgaaactg tttcggttcc tggatttcca gtgcttcaac ggtgggagac accgttaatt       540
ttgcagaatc atgagcaaat acagagccct tggtctcaga tgttgtttgg tcagtttgct       600
aatattgatc aagcacgttg ggtcttcaca atagttttt  acaagctcga ggaagaggta       660
atagagtgga cgagaaagat atggaacttg aaggtaatcg gccaacact  tccatccatg       720 taccttgaca acgacttga  tgatgataaa gataacggat ttaatctcta caaagcaaac       780
catcatgagt gcatgaactg gttagacgat aagccaaagg aatcagttgt ttacgtagca       840
tttggtagcc tggtgaaaca tggacccgaa caagtggaag aaatcacacg ggctttaata       900
gatagtgatg tcaacttctt gtgggttatc aaacataaag aagagggaaa gctcccagaa       960
aatctttcgg aagtaataaa aaccggaaag ggtttgattg tagcatggtg caaacaattg      1020
gatgtgttag cacacgaatc agtaggatgc tttgttacac attgtgggtt caactcaact      1080
cttgaagcaa taagtcttgg agtccccgtt gttgcaatgc ctcaattttc ggatcaaact      1140
acaaatgcca agcttctaga tgaaattttg ggtgttggag ttagagttaa gctgatgag       1200 aatgggatag tgagaagagg aaatcttgcg tcatgtatta gatgattat ggaggaggaa       1260
```

-continued

```
agaggagtaa taatccgaaa gaatgcggta aaatggaagg atttggctaa agtagccgtt    1320
catgaaggtg gtagctcaga caatgatatt gtcgaatttg taagtgagct aattaaggct    1380
taa                                                                  1383
```

<210> SEQ ID NO 3
<211> LENGTH: 490
<212> TYPE: PRT
<213> ORGANISM: Stevia rebaudiana

<400> SEQUENCE: 3

```
Met Ala Gly Ser His His His His His Gly Met Ala Ser Met Thr
1               5                   10                  15

Gly Gly Gln Gln Met Gly Arg Ser Gly Asp Asp Asp Lys Met Ala
            20                  25                  30

Glu Gln Gln Lys Ile Lys Lys Ser Pro His Val Leu Leu Ile Pro Phe
        35                  40                  45

Pro Leu Gln Gly His Ile Asn Pro Phe Ile Gln Phe Gly Lys Arg Leu
    50                  55                  60

Ile Ser Lys Gly Val Lys Thr Thr Leu Val Thr Thr Ile His Thr Leu
65                  70                  75                  80

Asn Ser Thr Leu Asn His Ser Asn Thr Thr Thr Ser Ile Glu Ile
                85                  90                  95

Gln Ala Ile Ser Asp Gly Cys Asp Glu Gly Gly Phe Met Ser Ala Gly
                100                 105                 110

Glu Ser Tyr Leu Glu Thr Phe Lys Gln Val Gly Ser Lys Ser Leu Ala
            115                 120                 125

Asp Leu Ile Lys Lys Leu Gln Ser Glu Gly Thr Thr Ile Asp Ala Ile
    130                 135                 140

Ile Tyr Asp Ser Met Thr Glu Trp Val Leu Asp Val Ala Ile Glu Phe
145                 150                 155                 160

Gly Ile Asp Gly Gly Ser Phe Phe Thr Gln Ala Cys Val Val Asn Ser
                165                 170                 175

Leu Tyr Tyr His Val His Lys Gly Leu Ile Ser Leu Pro Leu Gly Glu
            180                 185                 190

Thr Val Ser Val Pro Gly Phe Pro Val Leu Gln Arg Trp Glu Thr Pro
        195                 200                 205

Leu Ile Leu Gln Asn His Glu Gln Ile Gln Ser Pro Trp Ser Gln Met
    210                 215                 220

Leu Phe Gly Gln Phe Ala Asn Ile Asp Gln Ala Arg Trp Val Phe Thr
225                 230                 235                 240

Asn Ser Phe Tyr Lys Leu Glu Glu Val Ile Glu Trp Thr Arg Lys
                245                 250                 255

Ile Trp Asn Leu Lys Val Ile Gly Pro Thr Leu Pro Ser Met Tyr Leu
            260                 265                 270

Asp Lys Arg Leu Asp Asp Lys Asp Asn Gly Phe Asn Leu Tyr Lys
        275                 280                 285

Ala Asn His His Glu Cys Met Asn Trp Leu Asp Asp Lys Pro Lys Glu
    290                 295                 300

Ser Val Val Tyr Val Ala Phe Gly Ser Leu Val Lys His Gly Pro Glu
305                 310                 315                 320

Gln Val Glu Glu Ile Thr Arg Ala Leu Ile Asp Ser Asp Val Asn Phe
                325                 330                 335

Leu Trp Val Ile Lys His Lys Glu Glu Gly Lys Leu Pro Glu Asn Leu
```

```
              340             345             350
Ser Glu Val Ile Lys Thr Gly Lys Gly Leu Ile Val Ala Trp Cys Lys
            355                 360                 365

Gln Leu Asp Val Leu Ala His Glu Ser Val Gly Cys Phe Val Thr His
        370                 375                 380

Cys Gly Phe Asn Ser Thr Leu Glu Ala Ile Ser Leu Gly Val Pro Val
385                 390                 395                 400

Val Ala Met Pro Gln Phe Ser Asp Gln Thr Thr Asn Ala Lys Leu Leu
                405                 410                 415

Asp Glu Ile Leu Gly Val Gly Val Arg Val Lys Ala Asp Glu Asn Gly
            420                 425                 430

Ile Val Arg Arg Gly Asn Leu Ala Ser Cys Ile Lys Met Ile Met Glu
        435                 440                 445

Glu Glu Arg Gly Val Ile Ile Arg Lys Asn Ala Val Lys Trp Lys Asp
    450                 455                 460

Leu Ala Lys Val Ala Val His Glu Gly Gly Ser Ser Asp Asn Asp Ile
465                 470                 475                 480

Val Glu Phe Val Ser Glu Leu Ile Lys Ala
                485                 490

<210> SEQ ID NO 4
<211> LENGTH: 1473
<212> TYPE: DNA
<213> ORGANISM: Stevia rebaudiana

<400> SEQUENCE: 4
atggcgggtt ctcatcatca tcatcatcat ggtatggcta gcatgactgg tggacagcaa      60
atgggtcgct ccggtgatga tgatgacaag atggcggaac aacaaaagat caagaaatca     120
ccacacgttc tactcatccc attcccttta caaggccata taaaccccttt catccagttt     180 ggcaaacgat taatctccaa aggtgtcaaa acaacacttg ttaccaccat ccacacctta     240
aactcaaccc taaaccacag taacaccacc accacctcca tcgaaatcca agcaatttcc     300
gatggttgtg atgaaggcgg ttttatgagt gcaggagaat catatttgga acattcaaa     360 caagttgggt ctaaatcact agctgactta atcaagaagc ttcaaagtga aggaaccaca     420
attgatgcaa tcatttatga ttctatgact gaatgggttt tagatgttgc aattgagttt     480
ggaatcgatg tggttcgtt tttcactcaa gcttgtgttg taaacagctt atattatcat     540
gttcataagg gtttgatttc tttgccattg ggtgaaactg tttcggttcc tggatttcca     600
gtgcttcaac ggtgggagac accgttaatt ttgcagaatc atgagcaaat acagagccct     660
tggtctcaga tgttgtttgg tcagtttgct aatattgatc aagcacgttg ggtcttcaca     720
aatagttttt acaagctcga ggaagaggta atagagtgga cgagaaagat atggaacttg     780
aaggtaatcg ggccaacact tccatccatg taccttgaca aacgacttga tgatgataaa     840
gataacggat ttaatctcta caaagcaaac catcatgagt gcatgaactg gttagacgat     900
aagccaaagg aatcagttgt ttacgtagca tttggtagcc tggtgaaaca tggacccgaa     960
caagtggaag aaatcacacg ggctttaata gatagtgatg tcaacttctt gtgggttatc    1020
aaacataaag aagagggaaa gctcccagaa aatctttcgg aagtaataaa aaccggaaag    1080
ggtttgattg tagcatggtg caaacaattg gatgtgttag cacacgaatc agtaggatgc    1140
tttgttacac attgtgggtt caactcaact cttgaagcaa taagtcttgg agtccccgtt    1200
gttgcaatgc ctcaattttc ggatcaaact acaaatgcca agcttctaga tgaaattttg    1260
```

```
ggtgttggag ttagagttaa ggctgatgag aatgggatag tgagaagagg aaatcttgcg    1320
tcatgtatta agatgattat ggaggaggaa agaggagtaa taatccgaaa gaatgcggta    1380
aaatggaagg atttggctaa agtagccgtt catgaaggtg gtagctcaga caatgatatt    1440
gtcgaatttg taagtgagct aattaaggct taa                                 1473
```

<210> SEQ ID NO 5
<211> LENGTH: 458
<212> TYPE: PRT
<213> ORGANISM: Stevia rebaudiana

<400> SEQUENCE: 5

```
Met Glu Asn Lys Thr Glu Thr Thr Val Arg Arg Arg Arg Ile Ile
1               5                  10                  15

Leu Phe Pro Val Pro Phe Gln Gly His Ile Asn Pro Ile Leu Gln Leu
                20                  25                  30

Ala Asn Val Leu Tyr Ser Lys Gly Phe Ser Ile Thr Ile Phe His Thr
            35                  40                  45

Asn Phe Asn Lys Pro Lys Thr Ser Asn Tyr Pro His Phe Thr Phe Arg
        50                  55                  60

Phe Ile Leu Asp Asn Asp Pro Gln Asp Glu Arg Ile Ser Asn Leu Pro
65                  70                  75                  80

Thr His Gly Pro Leu Ala Gly Met Arg Ile Pro Ile Ile Asn Glu His
                85                  90                  95

Gly Ala Asp Glu Leu Arg Arg Glu Leu Glu Leu Leu Met Leu Ala Ser
            100                 105                 110

Glu Glu Asp Glu Glu Val Ser Cys Leu Ile Thr Asp Ala Leu Trp Tyr
        115                 120                 125

Phe Ala Gln Ser Val Ala Asp Ser Leu Asn Leu Arg Arg Leu Val Leu
    130                 135                 140

Met Thr Ser Ser Leu Phe Asn Phe His Ala His Val Ser Leu Pro Gln
145                 150                 155                 160

Phe Asp Glu Leu Gly Tyr Leu Asp Pro Asp Asp Lys Thr Arg Leu Glu
                165                 170                 175

Glu Gln Ala Ser Gly Phe Pro Met Leu Lys Val Lys Asp Ile Lys Ser
            180                 185                 190

Ala Tyr Ser Asn Trp Gln Ile Leu Lys Glu Ile Leu Gly Lys Met Ile
        195                 200                 205

Lys Gln Thr Lys Ala Ser Ser Gly Val Ile Trp Asn Ser Phe Lys Glu
    210                 215                 220

Leu Glu Glu Ser Glu Leu Glu Thr Val Ile Arg Glu Ile Pro Ala Pro
225                 230                 235                 240

Ser Phe Leu Ile Pro Leu Pro Lys His Leu Thr Ala Ser Ser Ser Ser
                245                 250                 255

Leu Leu Asp His Asp Arg Thr Val Phe Gln Trp Leu Asp Gln Gln Pro
            260                 265                 270

Pro Ser Ser Val Leu Tyr Val Ser Phe Gly Ser Thr Ser Glu Val Asp
        275                 280                 285

Glu Lys Asp Phe Leu Glu Ile Ala Arg Gly Leu Val Asp Ser Lys Gln
    290                 295                 300

Ser Phe Leu Trp Val Val Arg Pro Gly Phe Val Lys Gly Ser Thr Trp
305                 310                 315                 320

Val Glu Pro Leu Pro Asp Gly Phe Leu Gly Glu Arg Gly Arg Ile Val
                325                 330                 335
```

```
Lys Trp Val Pro Gln Gln Glu Val Leu Ala His Gly Ala Ile Gly Ala
              340                 345                 350

Phe Trp Thr His Ser Gly Trp Asn Ser Thr Leu Glu Ser Val Cys Glu
          355                 360                 365

Gly Val Pro Met Ile Phe Ser Asp Phe Gly Leu Asp Gln Pro Leu Asn
      370                 375                 380

Ala Arg Tyr Met Ser Asp Val Leu Lys Val Gly Val Tyr Leu Glu Asn
385                 390                 395                 400

Gly Trp Glu Arg Gly Glu Ile Ala Asn Ala Ile Arg Arg Val Met Val
              405                 410                 415

Asp Glu Glu Gly Glu Tyr Ile Arg Gln Asn Ala Arg Val Leu Lys Gln
              420                 425                 430

Lys Ala Asp Val Ser Leu Met Lys Gly Gly Ser Ser Tyr Glu Ser Leu
              435                 440                 445

Glu Ser Leu Val Ser Tyr Ile Ser Ser Leu
              450                 455

<210> SEQ ID NO 6
<211> LENGTH: 1377
<212> TYPE: DNA
<213> ORGANISM: Stevia rebaudiana

<400> SEQUENCE: 6
atggaaaata aaacggagac caccgttcgc cggcgccgga gaataatatt attcccggta      60
ccatttcaag gccacattaa cccaattctt cagctagcca atgtgttgta ctctaaagga     120
ttcagtatca ccatctttca caccaacttc aacaaaccca aacatctaa ttaccctcac      180 ttcactttca gattcatcct cgacaacgac ccacaagacg aacgcatttc caatctaccg     240
actcatggtc cgctcgctgg tatgcggatt ccgattatca cgaacacgg agctgacgaa      300 ttacgacgcg aactggaact gttgatgtta gcttctgaag aagatgaaga ggtatcgtgt     360
ttaatcacgg atgctctttg gtacttcgcg caatctgttg ctgacagtct taacctccga     420
cggcttgttt tgatgacaag cagcttgttt aattttcatg cacatgtttc acttcctcag     480
tttgatgagc ttggttacct cgatcctgat gacaaaaccc gtttggaaga caagcgagt      540 gggtttccta tgctaaaagt gaaagacatc aagtctgcgt attcgaactg gcaaatactc     600
aaagagatat tagggaagat gataaaacaa acaaaagcat cttcaggagt catctggaac     660
tcatttaagg aactcgaaga gtctgagctc gaaactgtta tccgtgagat cccggctcca     720
agttccttga taccactccc caagcatttg acagcctctt ccagcagctt actagaccac     780
gatcgaaccg ttttcaatg gttagaccaa caaccgccaa gttcggtact gtatgttagt      840
tttggtagta ctagtgaagt ggatgagaaa gatttcttgg aaatagctcg tgggttggtt     900
gatagcaagc agtcgttttt atgggtggtt cgacctgggt ttgtcaaggg ttcgacgtgg     960
gtcgaaccgt tgccagatgg gttcttgggt gaaagaggac gtattgtgaa atgggttcca    1020
cagcaagaag tgctagctca tggagcaata ggcgcattct ggactcatag cggatggaac    1080
tctacgttgg aaagcgtttg tgaaggtgtt cctatgattt tctcggattt tgggctcgat    1140
caaccgttga atgctagata catgagtgat gttttgaagg tagggggtgta tttggaaaat    1200 gggtgggaaa gaggagagat agcaaatgca ataagaagag ttatggtgga tgaagaagga    1260
gaatacatta gacagaatgc aagagttttg aaacaaaagg cagatgtttc tttgatgaag    1320
ggtggttcgt cttacgaatc attagagtct ctagtttctt acatttcatc gttgtaa       1377
```

<210> SEQ ID NO 7
<211> LENGTH: 481
<212> TYPE: PRT
<213> ORGANISM: Stevia rebaudiana

<400> SEQUENCE: 7

Met Asp Ala Met Ala Thr Thr Glu Lys Lys Pro His Val Ile Phe Ile
1               5                   10                  15

Pro Phe Pro Ala Gln Ser His Ile Lys Ala Met Leu Lys Leu Ala Gln
            20                  25                  30

Leu Leu His His Lys Gly Leu Gln Ile Thr Phe Val Asn Thr Asp Phe
        35                  40                  45

Ile His Asn Gln Phe Leu Glu Ser Ser Gly Pro His Cys Leu Asp Gly
    50                  55                  60

Ala Pro Gly Phe Arg Phe Glu Thr Ile Pro Asp Gly Val Ser His Ser
65                  70                  75                  80

Pro Glu Ala Ser Ile Pro Ile Arg Glu Ser Leu Leu Arg Ser Ile Glu
                85                  90                  95

Thr Asn Phe Leu Asp Arg Phe Ile Asp Leu Val Thr Lys Leu Pro Asp
            100                 105                 110

Pro Pro Thr Cys Ile Ile Ser Asp Gly Phe Leu Ser Val Phe Thr Ile
        115                 120                 125

Asp Ala Ala Lys Lys Leu Gly Ile Pro Val Met Met Tyr Trp Thr Leu
130                 135                 140

Ala Ala Cys Gly Phe Met Gly Phe Tyr His Ile His Ser Leu Ile Glu
145                 150                 155                 160

Lys Gly Phe Ala Pro Leu Lys Asp Ala Ser Tyr Leu Thr Asn Gly Tyr
                165                 170                 175

Leu Asp Thr Val Ile Asp Trp Val Pro Gly Met Glu Gly Ile Arg Leu
            180                 185                 190

Lys Asp Phe Pro Leu Asp Trp Ser Thr Asp Leu Asn Asp Lys Val Leu
        195                 200                 205

Met Phe Thr Thr Glu Ala Pro Gln Arg Ser His Lys Val Ser His His
    210                 215                 220

Ile Phe His Thr Phe Asp Glu Leu Glu Pro Ser Ile Ile Lys Thr Leu
225                 230                 235                 240

Ser Leu Arg Tyr Asn His Ile Tyr Thr Ile Gly Pro Leu Gln Leu Leu
                245                 250                 255

Leu Asp Gln Ile Pro Glu Glu Lys Lys Gln Thr Gly Ile Thr Ser Leu
            260                 265                 270

His Gly Tyr Ser Leu Val Lys Glu Glu Pro Glu Cys Phe Gln Trp Leu
        275                 280                 285

Gln Ser Lys Glu Pro Asn Ser Val Val Tyr Val Asn Phe Gly Ser Thr
    290                 295                 300

Thr Val Met Ser Leu Glu Asp Met Thr Glu Phe Gly Trp Gly Leu Ala
305                 310                 315                 320

Asn Ser Asn His Tyr Phe Leu Trp Ile Ile Arg Ser Asn Leu Val Ile
                325                 330                 335

Gly Glu Asn Ala Val Leu Pro Pro Glu Leu Glu Glu His Ile Lys Lys
            340                 345                 350

Arg Gly Phe Ile Ala Ser Trp Cys Ser Gln Glu Lys Val Leu Lys His
        355                 360                 365

Pro Ser Val Gly Gly Phe Leu Thr His Cys Gly Trp Gly Ser Thr Ile
    370                 375                 380

```
Glu Ser Leu Ser Ala Gly Val Pro Met Ile Cys Trp Pro Tyr Ser Trp
385                 390                 395                 400

Asp Gln Leu Thr Asn Cys Arg Tyr Ile Cys Lys Glu Trp Glu Val Gly
                405                 410                 415

Leu Glu Met Gly Thr Lys Val Lys Arg Asp Glu Val Lys Arg Leu Val
            420                 425                 430

Gln Glu Leu Met Gly Glu Gly Gly His Lys Met Arg Asn Lys Ala Lys
        435                 440                 445

Asp Trp Lys Glu Lys Ala Arg Ile Ala Ile Ala Pro Asn Gly Ser Ser
    450                 455                 460

Ser Leu Asn Ile Asp Lys Met Val Lys Glu Ile Thr Val Leu Ala Arg
465                 470                 475                 480

Asn
```

<210> SEQ ID NO 8
<211> LENGTH: 1446
<212> TYPE: DNA
<213> ORGANISM: Stevia rebaudiana

<400> SEQUENCE: 8

```
atggatgcaa tggctacaac tgagaagaaa ccacacgtca tcttcatacc atttccagca      60
caaagccaca ttaaagccat gctcaaacta gcacaacttc tccaccacaa aggactccag     120
ataaccttcg tcaacaccga cttcatccac aaccagtttc ttgaatcatc gggcccacat     180
tgtctagacg gtgcaccggg tttccggttc gaaaccattc ggatggtgt ttctcacagt     240
ccggaagcga gcatcccaat cagagaatca ctcttgagat ccattgaaac caacttcttg     300
gatcgtttca ttgatcttgt aaccaaactt ccggatcctc cgacttgtat tatctcagat     360
gggttcttgt cggttttcac aattgacgct gcaaaaaagc ttggaattcc ggtcatgatg     420
tattggacac ttgctgcctg tgggttcatg gttttttacc atattcattc tctcattgag     480
aaaggatttg caccacttaa agatgcaagt tacttgacaa tgggtatttt ggacaccgtc     540
attgattggg ttccgggaat ggaaggcatc cgtctcaagg atttcccgct ggactggagc     600
actgacctca tgacaaagt tttgatgttc actacggaag ctcctcaaag gtcacacaag     660
gtttcacatc atattttcca cacgttcgat gagttggagc ctagtattat aaaaactttg     720
tcattgaggt ataatcacat ttacaccatc ggcccactgc aattacttct tgatcaaata     780
cccgaagaga aaaagcaaac tggaattacg agtctccatg gatacagttt agtaaaagaa     840
gaaccagagt gtttccagtg gcttcagtct aaagaaccaa attccgtcgt ttatgtaaat     900
tttggaagta ctacagtaat gtctttagaa gacatgacgg aatttggttg gggacttgct     960
aatagcaacc attatttcct ttggatcatc cgatcaaact tggtgatagg ggaaaatgca    1020
gttttgcccc ctgaacttga ggaacatata agaaaagag gctttattgc tagctggtgt    1080
tcacaagaaa aggtcttgaa gcacccttcg gttggagggt tcttgactca ttgtgggtgg    1140
ggatcgacca tcgagagctt gtctgctggg gtgccaatga tatgctggcc ttattcgtgg    1200
gaccagctga ccaactgtag gtatatatgc aaagaatggg aggttgggct cgagatggga    1260
accaaagtga aacagagatga agtcaagagg cttgtacaag agttgatggg agaaggaggt    1320
cacaaaatga ggaacaaggc taagattgg aaagaaaagg ctcgcattgc aatagctcct    1380
aacggttcat cttcttttgaa catagacaaa atggtcaagg aaatcaccgt gctagcaaga    1440
aactag                                                               1446
```

```
<210> SEQ ID NO 9
<211> LENGTH: 473
<212> TYPE: PRT
<213> ORGANISM: Stevia rebaudiana

<400> SEQUENCE: 9
```

| | | | | | | | | | | | | | | |
|---|---|---|---|---|---|---|---|---|---|---|---|---|---|---|
| Met | Ala | Thr | Ser | Asp | Ser | Met | Gln | Asp | Asp | Arg | Lys | Gln | Leu | His | Val |
| 1 | | | | 5 | | | | | 10 | | | | | 15 | |

| Ala | Thr | Phe | Pro | Trp | Phe | Ala | Phe | Gly | His | Ile | Leu | Pro | Tyr | Leu | Gln |
|---|---|---|---|---|---|---|---|---|---|---|---|---|---|---|---|
| | | | 20 | | | | | 25 | | | | | 30 | | |

| Leu | Ser | Lys | Leu | Ile | Ala | Glu | Lys | Gly | His | Lys | Val | Ser | Phe | Leu | Ser |
|---|---|---|---|---|---|---|---|---|---|---|---|---|---|---|---|
| | | | 35 | | | | | 40 | | | | | 45 | | |

| Thr | Thr | Arg | Asn | Ile | Gln | Arg | Leu | Ser | Ser | His | Ile | Ser | Pro | Leu | Ile |
|---|---|---|---|---|---|---|---|---|---|---|---|---|---|---|---|
| | 50 | | | | | 55 | | | | | 60 | | | | |

| Asn | Val | Val | Gln | Leu | Thr | Leu | Pro | Arg | Val | Gln | Glu | Leu | Pro | Glu | Asp |
|---|---|---|---|---|---|---|---|---|---|---|---|---|---|---|---|
| 65 | | | | | 70 | | | | | 75 | | | | | 80 |

| Ala | Glu | Ala | Thr | Thr | Asp | Val | His | Pro | Glu | Asp | Ile | Pro | Tyr | Leu | Lys |
|---|---|---|---|---|---|---|---|---|---|---|---|---|---|---|---|
| | | | | 85 | | | | | 90 | | | | | 95 | |

| Lys | Ala | Ser | Asp | Gly | Leu | Gln | Pro | Glu | Val | Thr | Arg | Phe | Leu | Glu | Gln |
|---|---|---|---|---|---|---|---|---|---|---|---|---|---|---|---|
| | | | 100 | | | | | 105 | | | | | 110 | | |

| His | Ser | Pro | Asp | Trp | Ile | Ile | Tyr | Asp | Tyr | Thr | His | Tyr | Trp | Leu | Pro |
|---|---|---|---|---|---|---|---|---|---|---|---|---|---|---|---|
| | | | 115 | | | | | 120 | | | | | 125 | | |

| Ser | Ile | Ala | Ala | Ser | Leu | Gly | Ile | Ser | Arg | Ala | Tyr | Phe | Cys | Val | Ile |
|---|---|---|---|---|---|---|---|---|---|---|---|---|---|---|---|
| | 130 | | | | | 135 | | | | | 140 | | | | |

| Thr | Pro | Trp | Thr | Ile | Ala | Tyr | Met | Gly | Pro | Ser | Ala | Asp | Ala | Met | Ile |
|---|---|---|---|---|---|---|---|---|---|---|---|---|---|---|---|
| 145 | | | | | 150 | | | | | 155 | | | | | 160 |

| Asn | Gly | Ser | Asp | Gly | Arg | Thr | Thr | Val | Glu | Asp | Leu | Thr | Thr | Pro | Pro |
|---|---|---|---|---|---|---|---|---|---|---|---|---|---|---|---|
| | | | | 165 | | | | | 170 | | | | | 175 | |

| Lys | Trp | Phe | Pro | Phe | Pro | Thr | Lys | Val | Cys | Trp | Arg | Lys | His | Asp | Leu |
|---|---|---|---|---|---|---|---|---|---|---|---|---|---|---|---|
| | | | 180 | | | | | 185 | | | | | 190 | | |

| Ala | Arg | Leu | Val | Pro | Tyr | Lys | Ala | Pro | Gly | Ile | Ser | Asp | Gly | Tyr | Arg |
|---|---|---|---|---|---|---|---|---|---|---|---|---|---|---|---|
| | | | 195 | | | | | 200 | | | | | 205 | | |

| Met | Gly | Leu | Val | Leu | Lys | Gly | Ser | Asp | Cys | Leu | Leu | Ser | Lys | Cys | Tyr |
|---|---|---|---|---|---|---|---|---|---|---|---|---|---|---|---|
| | 210 | | | | | 215 | | | | | 220 | | | | |

| His | Glu | Phe | Gly | Thr | Gln | Trp | Leu | Pro | Leu | Leu | Glu | Thr | Leu | His | Gln |
|---|---|---|---|---|---|---|---|---|---|---|---|---|---|---|---|
| 225 | | | | | 230 | | | | | 235 | | | | | 240 |

| Val | Pro | Val | Val | Pro | Val | Gly | Leu | Leu | Pro | Pro | Glu | Ile | Pro | Gly | Asp |
|---|---|---|---|---|---|---|---|---|---|---|---|---|---|---|---|
| | | | | 245 | | | | | 250 | | | | | 255 | |

| Glu | Lys | Asp | Glu | Thr | Trp | Val | Ser | Ile | Lys | Lys | Trp | Leu | Asp | Gly | Lys |
|---|---|---|---|---|---|---|---|---|---|---|---|---|---|---|---|
| | | | 260 | | | | | 265 | | | | | 270 | | |

| Gln | Lys | Gly | Ser | Val | Val | Tyr | Val | Ala | Leu | Gly | Ser | Glu | Val | Leu | Val |
|---|---|---|---|---|---|---|---|---|---|---|---|---|---|---|---|
| | | 275 | | | | | 280 | | | | | 285 | | | |

| Ser | Gln | Thr | Glu | Val | Val | Glu | Leu | Ala | Leu | Gly | Leu | Glu | Leu | Ser | Gly |
|---|---|---|---|---|---|---|---|---|---|---|---|---|---|---|---|
| | 290 | | | | | 295 | | | | | 300 | | | | |

| Leu | Pro | Phe | Val | Trp | Ala | Tyr | Arg | Lys | Pro | Lys | Gly | Pro | Ala | Lys | Ser |
|---|---|---|---|---|---|---|---|---|---|---|---|---|---|---|---|
| 305 | | | | | 310 | | | | | 315 | | | | | 320 |

| Asp | Ser | Val | Glu | Leu | Pro | Asp | Gly | Phe | Val | Glu | Arg | Thr | Arg | Asp | Arg |
|---|---|---|---|---|---|---|---|---|---|---|---|---|---|---|---|
| | | | | 325 | | | | | 330 | | | | | 335 | |

| Gly | Leu | Val | Trp | Thr | Ser | Trp | Ala | Pro | Gln | Leu | Arg | Ile | Leu | Ser | His |
|---|---|---|---|---|---|---|---|---|---|---|---|---|---|---|---|
| | | | 340 | | | | | 345 | | | | | 350 | | |

| Glu | Ser | Val | Cys | Gly | Phe | Leu | Thr | His | Cys | Gly | Ser | Gly | Ser | Ile | Val |
|---|---|---|---|---|---|---|---|---|---|---|---|---|---|---|---|
| | | 355 | | | | | 360 | | | | | 365 | | | |

| Glu | Gly | Leu | Met | Phe | Gly | His | Pro | Leu | Ile | Met | Leu | Pro | Ile | Phe | Gly |
|---|---|---|---|---|---|---|---|---|---|---|---|---|---|---|---|
| | 370 | | | | | 375 | | | | | 380 | | | | |

```
Asp Gln Pro Leu Asn Ala Arg Leu Leu Glu Asp Lys Gln Val Gly Ile
385                 390                 395                 400

Glu Ile Pro Arg Asn Glu Glu Asp Gly Cys Leu Thr Lys Glu Ser Val
            405                 410                 415

Ala Arg Pro Leu Arg Ser Val Val Glu Lys Glu Gly Glu Ile Ser
        420                 425                 430

Lys Ala Asn Ala Arg Glu Leu Ser Lys Ile Tyr Asn Ala Thr Lys Val
        435                 440                 445

Glu Lys Glu Tyr Val Ser Gln Phe Val Asp Tyr Leu Glu Lys Asn Ala
    450                 455                 460

Arg Ala Val Ala Ile Asp His Glu Ser
465                 470

<210> SEQ ID NO 10
<211> LENGTH: 1422
<212> TYPE: DNA
<213> ORGANISM: Stevia rebaudiana

<400> SEQUENCE: 10
atggctacca gtgactccat gcaagacgac cggaagcagc ttcatgttgc gacgttccca      60
tggtttgctt tcggtcacat cctcccttac cttcagcttt cgaaattgat agctgaaaag     120
ggtcacaaag tctcgtttct ttctaccacc agaaacattc aacgtctctc ttctcatatc     180
tcgccactca taaatgttgt tcaactcaca cttccacgtg tccaagagct gccggaggat     240
gcagaggcga ccactgacgt ccaccctgaa gatattccat atctcaagaa ggcttctgat     300
ggtcttcaac cggaggtcac ccggtttcta gaacaacact ctccggactg gattattat       360 gattatactc actactggtt gccatccatc gcggctagcc tcggtatctc acgagcctac     420
ttctgcgtca tcactccatg gaccattgct tatatgggac cctcagctga cgccatgata     480
aatggttcag atggtcgaac cacggttgag gatctcacga caccgcccaa gtggtttccc     540
tttccgacca agtatgctg gcggaagcat gatcttgccc gactggtgcc ttacaaagct     600
ccggggatat ctgatggata ccgtatgggg ctggttctta agggatctga ttgtttgctt     660
tccaaatgtt accatgagtt tggaactcaa tggctacctc ttttggagac actcaccaa       720 gtaccggtgg ttccggtggg attactgcca ccggaaatac ccggagacga aaagatgaa       780 acatgggtgt caatcaagaa atggctcgat ggtaaacaaa aaggcagtgt ggtgtacgtt     840
gcattaggaa gcgaggtttt ggtgagccaa accgaggttg ttgagttagc attgggtctc     900
gagctttctg ggttgccatt tgtttgggct tatagaaaac caaaaggtcc cgcgaagtca     960
gactcggtgg agttgccaga cgggttcgtg aacgaactc gtgaccgtgg gttggtctgg    1020
acgagttggg caccgtcagtt acgaatactg agccatgagt cggtttgtgg tttcttgact    1080
cattgtggtt ctggatcaat tgtggaaggg ctaatgtttg gtcaccctct aatcatgcta    1140
ccgatttttg ggaccaacc tctgaatgct cgattactgg aggacaaaca ggtgggaatc    1200
gagataccaa gaaatgagga agatggttgc ttgaccaagg agtcggttgc tagaccactg    1260
aggtccgttg ttgtggaaaa agaaggggag atctccaagg cgaacgcgag ggagctgagt    1320
aaaatctata cgccactaa ggttgaaaaa gaatatgtaa gccaattcgt agactatttg      1380
gaaaagaatg cgcgtgcggt tgccatcgat catgagagtt aa                       1422

<210> SEQ ID NO 11
<211> LENGTH: 462
<212> TYPE: PRT
<213> ORGANISM: Oryza sativa
```

```
<400> SEQUENCE: 11

Met Asp Ser Gly Tyr Ser Ser Tyr Ala Ala Ala Gly Met His
1               5                   10                  15

Val Val Ile Cys Pro Trp Leu Ala Phe Gly His Leu Leu Pro Cys Leu
            20                  25                  30

Asp Leu Ala Gln Arg Leu Ala Ser Arg Gly His Arg Val Ser Phe Val
            35                  40                  45

Ser Thr Pro Arg Asn Ile Ser Arg Leu Pro Pro Val Arg Pro Ala Leu
            50                  55                  60

Ala Pro Leu Val Ala Phe Val Ala Leu Pro Leu Pro Arg Val Glu Gly
65                  70                  75                  80

Leu Pro Asp Gly Ala Glu Ser Thr Asn Asp Val Pro His Asp Arg Pro
                    85                  90                  95

Asp Met Val Glu Leu His Arg Arg Ala Phe Asp Gly Leu Ala Ala Pro
                100                 105                 110

Phe Ser Glu Phe Leu Gly Thr Ala Cys Ala Asp Trp Val Ile Val Asp
            115                 120                 125

Val Phe His His Trp Ala Ala Ala Ala Leu Glu His Lys Val Pro
130                 135                 140

Cys Ala Met Met Leu Leu Gly Ser Ala His Met Ile Ala Ser Ile Ala
145                 150                 155                 160

Asp Arg Arg Leu Glu Arg Ala Glu Thr Glu Ser Pro Ala Ala Gly
                165                 170                 175

Gln Gly Arg Pro Ala Ala Ala Pro Thr Phe Glu Val Ala Arg Met Lys
            180                 185                 190

Leu Ile Arg Thr Lys Gly Ser Ser Gly Met Ser Leu Ala Glu Arg Phe
            195                 200                 205

Ser Leu Thr Leu Ser Arg Ser Ser Leu Val Val Gly Arg Ser Cys Val
            210                 215                 220

Glu Phe Glu Pro Glu Thr Val Pro Leu Leu Ser Thr Leu Arg Gly Lys
225                 230                 235                 240

Pro Ile Thr Phe Leu Gly Leu Met Pro Pro Leu His Glu Gly Arg Arg
                245                 250                 255

Glu Asp Gly Glu Asp Ala Thr Val Arg Trp Leu Asp Ala Gln Pro Ala
                260                 265                 270

Lys Ser Val Val Tyr Val Ala Leu Gly Ser Glu Val Pro Leu Gly Val
            275                 280                 285

Glu Lys Val His Glu Leu Ala Leu Gly Leu Glu Leu Ala Gly Thr Arg
            290                 295                 300

Phe Leu Trp Ala Leu Arg Lys Pro Thr Gly Val Ser Asp Ala Asp Leu
305                 310                 315                 320

Leu Pro Ala Gly Phe Glu Glu Arg Thr Arg Gly Arg Gly Val Val Ala
                325                 330                 335

Thr Arg Trp Val Pro Gln Met Ser Ile Leu Ala His Ala Ala Val Gly
                340                 345                 350

Ala Phe Leu Thr His Cys Gly Trp Asn Ser Thr Ile Glu Gly Leu Met
            355                 360                 365

Phe Gly His Pro Leu Ile Met Leu Pro Ile Phe Gly Asp Gln Gly Pro
            370                 375                 380

Asn Ala Arg Leu Ile Glu Ala Lys Asn Ala Gly Leu Gln Val Ala Arg
385                 390                 395                 400

Asn Asp Gly Asp Gly Ser Phe Asp Arg Glu Gly Val Ala Ala Ala Ile
```

```
              405                 410                 415
Arg Ala Val Ala Val Glu Glu Glu Ser Ser Lys Val Phe Gln Ala Lys
        420                 425                 430

Ala Lys Lys Leu Gln Glu Ile Val Ala Asp Met Ala Cys His Glu Arg
        435                 440                 445

Tyr Ile Asp Gly Phe Ile Gln Gln Leu Arg Ser Tyr Lys Asp
        450                 455                 460

<210> SEQ ID NO 12
<211> LENGTH: 1389
<212> TYPE: DNA
<213> ORGANISM: Oryza sativa

<400> SEQUENCE: 12
atggatagcg gttatagctc tagttacgcg gctgcggccg ggatgcacgt tgtgatttgt      60
ccgtggctcg catttggcca tttgttgcct tgccttgatt tagcacagcg ccttgctagc     120
cgcggccatc gtgtgtcttt cgtgagcact ccacggaata tctcacgtct gccaccagtg     180
cgtcctgcgc tggctccact tgtggccttc gtggctctgc cgttaccgcg tgttgagggt     240
cttccggatg gagccgagtc aacaaacgac gttcctcacg accgtccgga catggttgaa     300
ctgcatcgcc gcgccttcga cggtttagcg gcacctttct cagaatttct cggtaccgct     360
tgtgcggact gggttattgt ggatgtcttc catcactggg cagcggcagc ggccctggaa     420
cacaaggtac cttgtgcaat gatgctgctg ggttcggcgc atatgattgc ctccatcgcc     480
gaccgtcgcc tcgaacgggc ggagacggaa tccccggcgg cggctggaca gggtcgcccg     540
gctgccgctc aacatttga agtggcccgc atgaagctta ttcgcaccaa aggatcctcg     600
ggtatgtctt tggccgagcg tttctcactg accttaagcc gcagctcttt ggtcgtgggg     660
cgcagctgcg tggaatttga accggagacg gtcccactgc tctcgacatt gcgtggtaaa     720
cccattactt tcctgggttt aatgccgcca ttacacgagg gccgtcgcga ggatggcgaa     780
gatgccaccg tacgttggct cgatgcacag cctgccaaat ctgtagttta cgtggcgctc     840
ggtagtgaag tcccgctcgg tgtggaaaag gttcacgaac tggccttagg cctggaactg     900
gcggggaccc gcttcttgtg ggcgctgcgt aaaccgacgg gcgtgtctga cgcggacttg     960
ctgccggcgg gtttcgaaga acgcacgcgt gggcgtggtg ttgtcgccac tcgtttgggtt    1020 cctcagatga gcattctcgc gcatgcggcc gtaggcgcct ttctcacgca ttgcgggtgg    1080
aactctacta ttgaggggct gatgtttggc catcctttga tcatgttacc gatcttcggt    1140
gaccaaggac ctaacgcgcg tttgattgag gccaagaatg cgggactgca ggtggcgcgt    1200
aacgatggcg acggatcttt cgaccgggaa ggtgttgccg cggccatccg tgccgttgcc    1260
gtggaagaag aaagtagtaa ggtattccag gcgaaggcga aaaaacttca ggaaattgtg    1320
gcagatatgg cctgccatga acgctatatt gatgggttta ttcaacagtt gcgttcttac    1380
aaagactga                                                            1389

<210> SEQ ID NO 13
<211> LENGTH: 37
<212> TYPE: DNA
<213> ORGANISM: Artificial sequence
<220> FEATURE:
<223> OTHER INFORMATION: Synthetic

<400> SEQUENCE: 13
agaaggagat ataactatgg cggaacaaca aaagatc                               37
```

<210> SEQ ID NO 14
<211> LENGTH: 46
<212> TYPE: DNA
<213> ORGANISM: Artificial sequence
<220> FEATURE:
<223> OTHER INFORMATION: Synthetic

<400> SEQUENCE: 14
ggagatggga agtcattatt aagccttaat tagctcactt acaaat            46

<210> SEQ ID NO 15
<211> LENGTH: 43
<212> TYPE: DNA
<213> ORGANISM: Artificial sequence
<220> FEATURE:
<223> OTHER INFORMATION: Synthetic

<400> SEQUENCE: 15
ggtgatgatg atgacaagat ggaaaataaa acggagacca ccg               43

<210> SEQ ID NO 16
<211> LENGTH: 51
<212> TYPE: DNA
<213> ORGANISM: Artificial sequence
<220> FEATURE:
<223> OTHER INFORMATION: Synthetic

<400> SEQUENCE: 16
ggagatggga agtcattatt acaacgatga aatgtaagaa actagagact c       51

<210> SEQ ID NO 17
<211> LENGTH: 40
<212> TYPE: DNA
<213> ORGANISM: Artificial sequence
<220> FEATURE:
<223> OTHER INFORMATION: Synthetic

<400> SEQUENCE: 17
ggtgatgatg atgacaagat ggatgcaatg gctacaactg                   40

<210> SEQ ID NO 18
<211> LENGTH: 41
<212> TYPE: DNA
<213> ORGANISM: Artificial sequence
<220> FEATURE:
<223> OTHER INFORMATION: Synthetic

<400> SEQUENCE: 18
ggagatggga agtcattact agtttcttgc tagcacggtg a                 41

<210> SEQ ID NO 19
<211> LENGTH: 38
<212> TYPE: DNA
<213> ORGANISM: Artificial sequence
<220> FEATURE:
<223> OTHER INFORMATION: Synthetic

<400> SEQUENCE: 19
ggtgatgatg atgacaagat ggctaccagt gactccat                     38

<210> SEQ ID NO 20
<211> LENGTH: 41
<212> TYPE: DNA
<213> ORGANISM: Artificial sequence
<220> FEATURE:
<223> OTHER INFORMATION: Synthetic -continued

```
<400> SEQUENCE: 20
ggagatggga agtcattatt aactctcatg atcgatggca a                    41

<210> SEQ ID NO 21
<211> LENGTH: 42
<212> TYPE: DNA
<213> ORGANISM: Artificial sequence
<220> FEATURE:
<223> OTHER INFORMATION: Synthetic

<400> SEQUENCE: 21
ggtgatgatg atgacaagat ggatagtggt tacagttctt ct                   42

<210> SEQ ID NO 22
<211> LENGTH: 45
<212> TYPE: DNA
<213> ORGANISM: Artificial sequence
<220> FEATURE:
<223> OTHER INFORMATION: Synthetic

<400> SEQUENCE: 22
ggagatggga agtcattatt agtctttgta tgatctaagc tgttg                45
```